United States Patent
Ohguri

(10) Patent No.: US 10,708,497 B2
(45) Date of Patent: Jul. 7, 2020

(54) CONTROL APPARATUS, CONTROL SYSTEM, CONTROL METHOD, MEDICAL IMAGING APPARATUS, MEDICAL IMAGING SYSTEM, AND IMAGING CONTROL METHOD FOR SWITCHING IMAGING MODES BASED ON COMMUNICATION STATE

(71) Applicant: CANON KABUSHIKI KAISHA, Tokyo (JP)

(72) Inventor: Hirokazu Ohguri, Funabashi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 355 days.

(21) Appl. No.: 14/966,341

(22) Filed: Dec. 11, 2015

(65) Prior Publication Data
US 2016/0174927 A1   Jun. 23, 2016

(30) Foreign Application Priority Data
Dec. 17, 2014 (JP) .................. 2014-255441

(51) Int. Cl.
*H04N 5/232* (2006.01)
*A61B 6/00* (2006.01)
*G05B 15/02* (2006.01)

(52) U.S. Cl.
CPC ....... *H04N 5/23245* (2013.01); *A61B 6/4233* (2013.01); *A61B 6/563* (2013.01); *G05B 15/02* (2013.01)

(58) Field of Classification Search
None
See application file for complete search history.

(56) References Cited

U.S. PATENT DOCUMENTS 5,976,088 A * 11/1999 Urbano .................. A61B 8/543
                                              600/443
6,727,949 B1 * 4/2004 Saruwatari ......... H04N 5/23212
                                              348/349

(Continued)

FOREIGN PATENT DOCUMENTS

CN    103592673 A  *  2/2014  ............... H04N 5/32
JP    2009-272673 A     11/2009

(Continued)

OTHER PUBLICATIONS

JP Office Action dated Sep. 10, 2018 in corresponding JP Patent Application No. 2014-255441, with English translation.

*Primary Examiner* — Jayanti K Patel
*Assistant Examiner* — Stefan Gadomski
(74) *Attorney, Agent, or Firm* — Carter, DeLuca & Farrell LLP

(57) ABSTRACT

A control apparatus that controls medical imaging, includes: a communication unit configured to communicate with an imaging unit via a communication path that includes a wireless channel; an imaging control unit configured to cause the imaging unit to execute a plurality of imaging modes including a first imaging mode and a second imaging mode which obtains a larger data amount from imaging than the first imaging mode; a restricting unit configured to restrict transition of the imaging mode when a value indicating the state of communication with the imaging unit by the communication unit is smaller than a threshold; and a setting unit configured to set different threshold values for a case in which the first imaging mode transits to the second imaging mode and a case in which the second imaging mode transits to the first imaging mode.

13 Claims, 15 Drawing Sheets

(56) References Cited

U.S. PATENT DOCUMENTS

| | | | |
|---|---|---|---|
| 8,527,649 B2 * | 9/2013 | Wexler | H04L 65/4076 709/203 |
| 8,817,065 B1 * | 8/2014 | Mo | G06F 3/04842 348/14.08 |
| 9,106,887 B1 * | 8/2015 | Owen | H04N 19/102 |
| 9,295,076 B2 * | 3/2016 | MacInnis | H04W 72/1252 |
| 9,838,912 B1 * | 12/2017 | Pawar | H04W 36/0022 |
| 2002/0050940 A1 * | 5/2002 | Sato | H04N 1/195 341/155 |
| 2002/0144276 A1 * | 10/2002 | Radford | H04N 7/17318 725/87 |
| 2005/0094646 A1 * | 5/2005 | Lee | H04L 29/06027 370/395.52 |
| 2006/0244627 A1 * | 11/2006 | Kagermeier | G08C 17/02 340/13.25 |
| 2007/0011683 A1 * | 1/2007 | Helander | G06F 9/4887 718/104 |
| 2007/0067485 A1 * | 3/2007 | Stotland | H04L 29/06027 709/232 |
| 2007/0174881 A1 * | 7/2007 | Idehara | H04L 29/06027 725/90 |
| 2007/0237402 A1 * | 10/2007 | Dekel | G06F 19/321 382/232 |
| 2008/0013613 A1 * | 1/2008 | Ahmad | H04L 41/5003 375/224 |
| 2008/0144906 A1 * | 6/2008 | Allred | A61B 5/0059 382/131 |
| 2009/0238073 A1 * | 9/2009 | Sanjeewa | H04L 43/0882 370/235 |
| 2009/0272909 A1 * | 11/2009 | Takenaka | G01T 1/2928 250/370.09 |
| 2010/0250766 A1 * | 9/2010 | Riggert | H04N 21/234318 709/231 |
| 2011/0058036 A1 * | 3/2011 | Metzger | H04N 7/181 348/143 |
| 2011/0078231 A1 * | 3/2011 | Oliver | G06F 9/5055 709/203 |
| 2011/0080942 A1 * | 4/2011 | Nagara | H04L 1/0014 375/240.01 |
| 2011/0138427 A1 * | 6/2011 | Shen | H04N 7/18 725/62 |
| 2011/0188498 A1 * | 8/2011 | Inagaki | H04L 12/56 370/389 |
| 2011/0279640 A1 * | 11/2011 | Choi | H04N 7/148 348/14.12 |
| 2012/0195356 A1 * | 8/2012 | Yi | H04N 19/119 375/224 |
| 2012/0224484 A1 * | 9/2012 | Babiarz | H04L 41/5019 370/235 |
| 2013/0097220 A1 * | 4/2013 | Lyons | H04L 65/607 709/203 |
| 2013/0176848 A1 * | 7/2013 | Jinzaki | H04L 47/193 370/230.1 |
| 2013/0193339 A1 * | 8/2013 | Oda | G01T 1/17 250/394 |
| 2013/0208080 A1 * | 8/2013 | Lukasik | H04N 7/15 348/14.09 |
| 2014/0078246 A1 * | 3/2014 | Carpenter | H04N 7/148 348/14.13 |
| 2014/0129676 A1 * | 5/2014 | Zeng | H04W 4/18 709/217 |
| 2014/0160136 A1 * | 6/2014 | Kaburlasos | G09G 5/00 345/520 |
| 2014/0189091 A1 * | 7/2014 | Tamasi | H04L 43/0858 709/224 |
| 2014/0198838 A1 * | 7/2014 | Andrysco | H04N 19/172 375/240.1 |
| 2014/0219251 A1 * | 8/2014 | Kato | H04W 36/023 370/331 |
| 2014/0274078 A1 * | 9/2014 | Hyde | H04W 16/18 455/446 |
| 2014/0281023 A1 * | 9/2014 | Apte | H04L 69/02 709/235 |
| 2014/0286438 A1 * | 9/2014 | Apte | H04N 21/2343 375/240.26 |
| 2014/0289423 A1 * | 9/2014 | Kim | H04L 65/80 709/233 |
| 2015/0078522 A1 * | 3/2015 | Makino | G16H 40/63 378/62 |
| 2015/0078527 A1 * | 3/2015 | Iwamoto | A61B 6/563 378/91 |
| 2015/0078529 A1 * | 3/2015 | Tsubota | H04W 76/10 378/98 |
| 2015/0310597 A1 | 10/2015 | Ohguri et al. | |
| 2015/0350611 A1 * | 12/2015 | Pearson | H04L 67/10 348/158 |
| 2015/0381931 A1 * | 12/2015 | Uhma | H04N 7/147 348/14.03 |
| 2016/0036674 A1 * | 2/2016 | Tanaka | H04W 76/30 370/252 |
| 2016/0173805 A1 * | 6/2016 | Claus | H04N 17/004 348/148 |
| 2016/0182849 A1 * | 6/2016 | Wakao | H04N 7/18 348/333.04 |
| 2016/0212674 A1 * | 7/2016 | Nakamura | H04W 36/30 |
| 2017/0281115 A1 * | 10/2017 | Julien | A61B 6/145 |

FOREIGN PATENT DOCUMENTS

| | | |
|---|---|---|
| JP | 4519131 B2 | 8/2010 |
| JP | 2011-041866 A | 3/2011 |
| JP | 2013153790 A | 8/2013 |

* cited by examiner

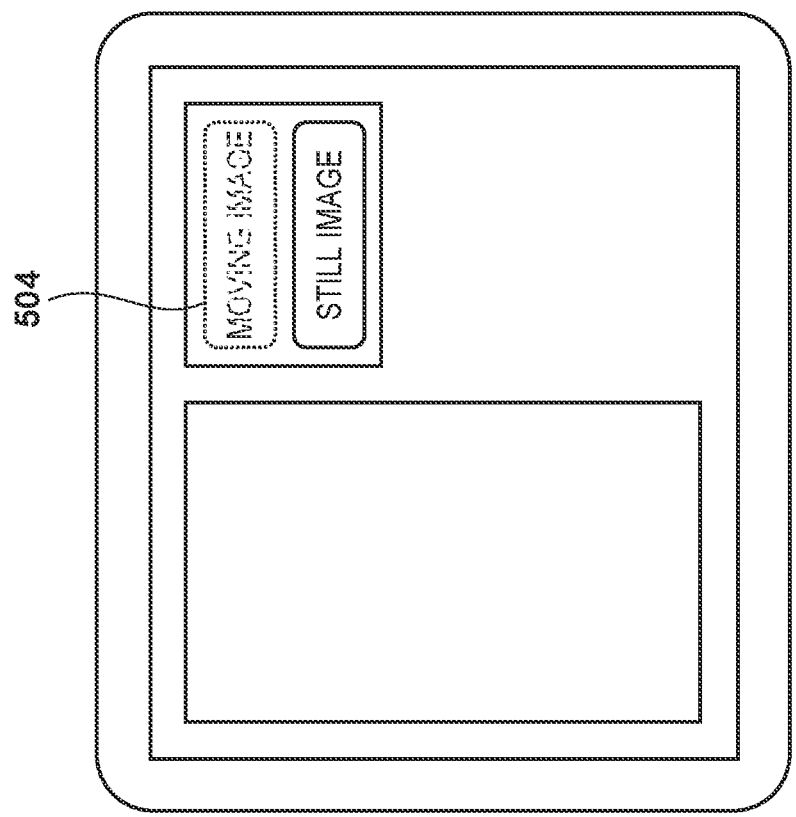
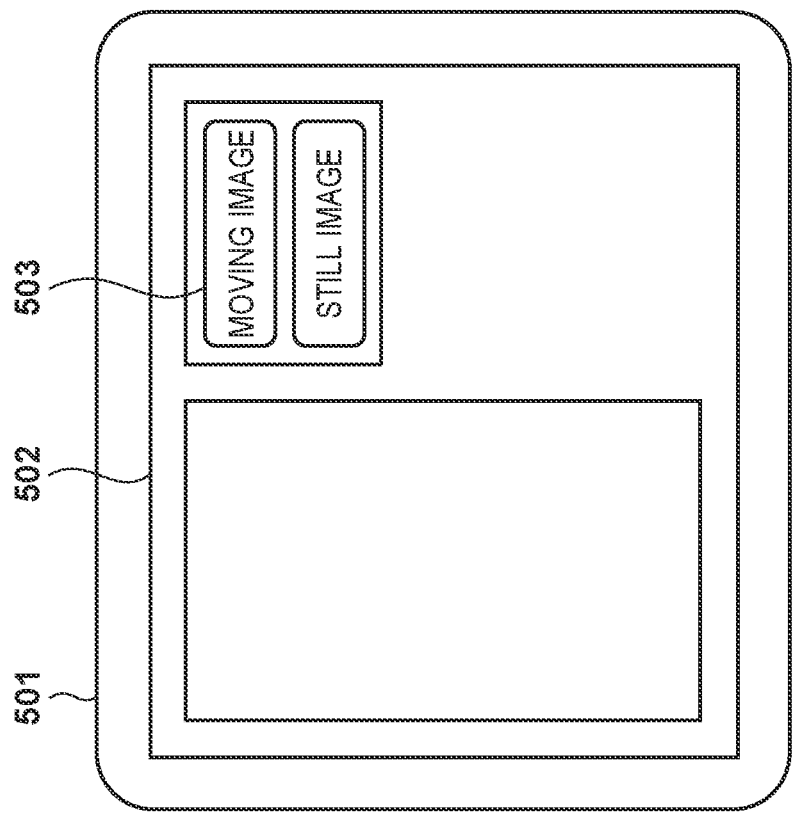

FIG. 7

| IMAGE SIZE | FRAME RATE | MINIMUM COMMUNICATION RATE |
|---|---|---|
| ... | ... | ... |
| 1000pix×1000pix | 10fps | 152Mbps |
| 1000pix×1000pix | 5fps | 76Mbps |
| 500pix×500pix | 10fps | 38Mbps |
| 1000pix×1000pix | 2fps | 30Mbps |
| 500pix×500pix | 2fps | 7.5Mbps |
| ... | ... | ... |

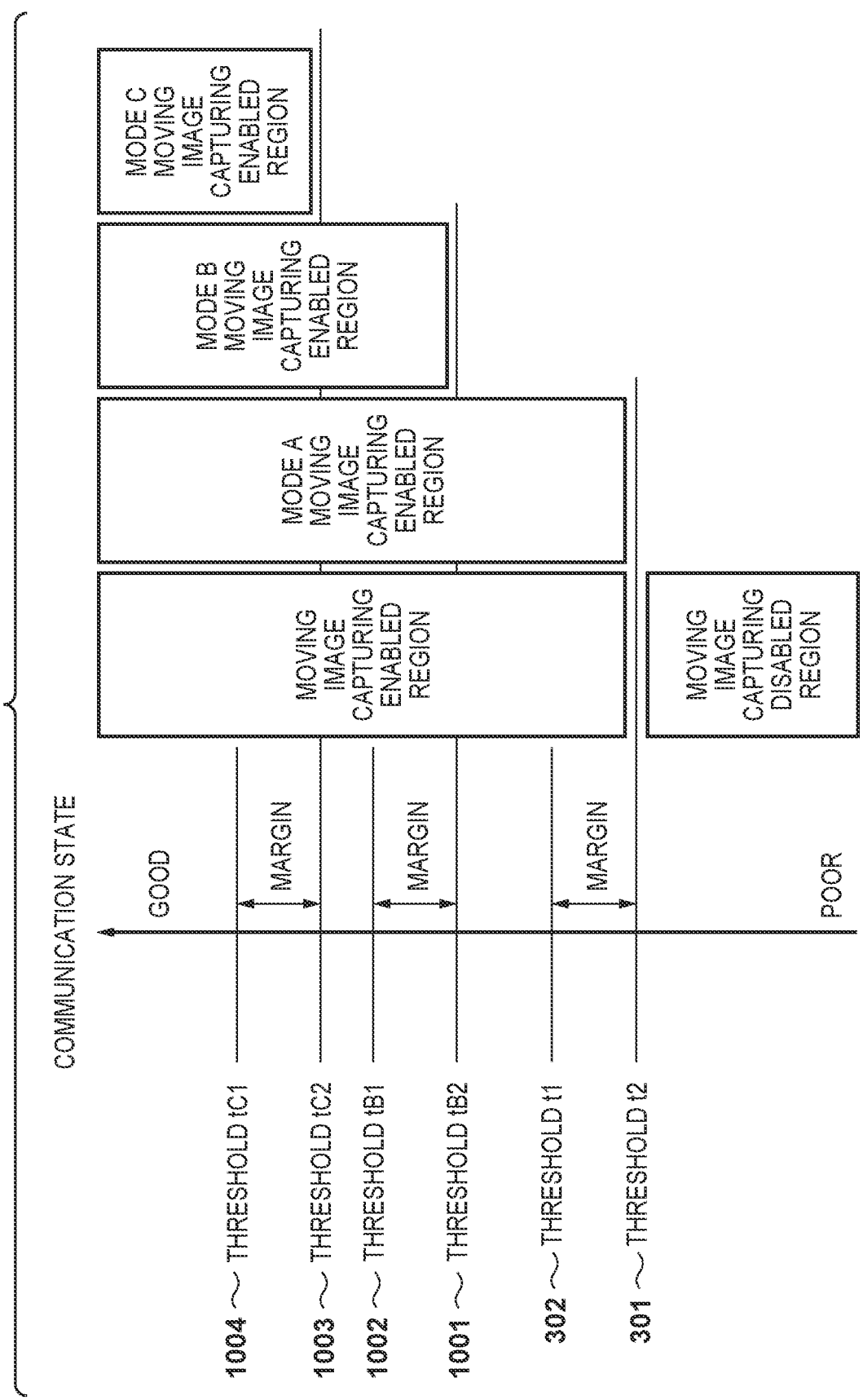

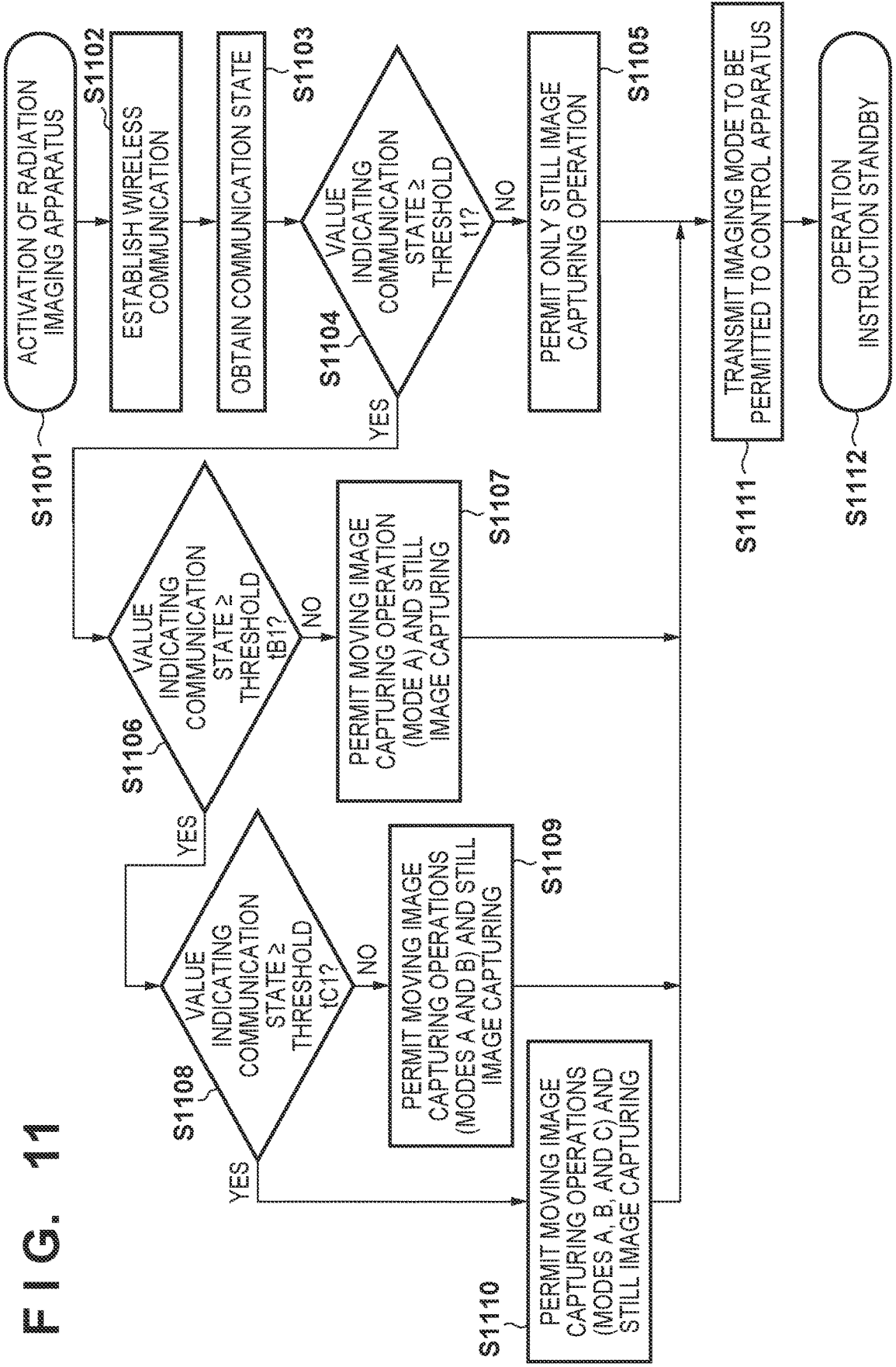

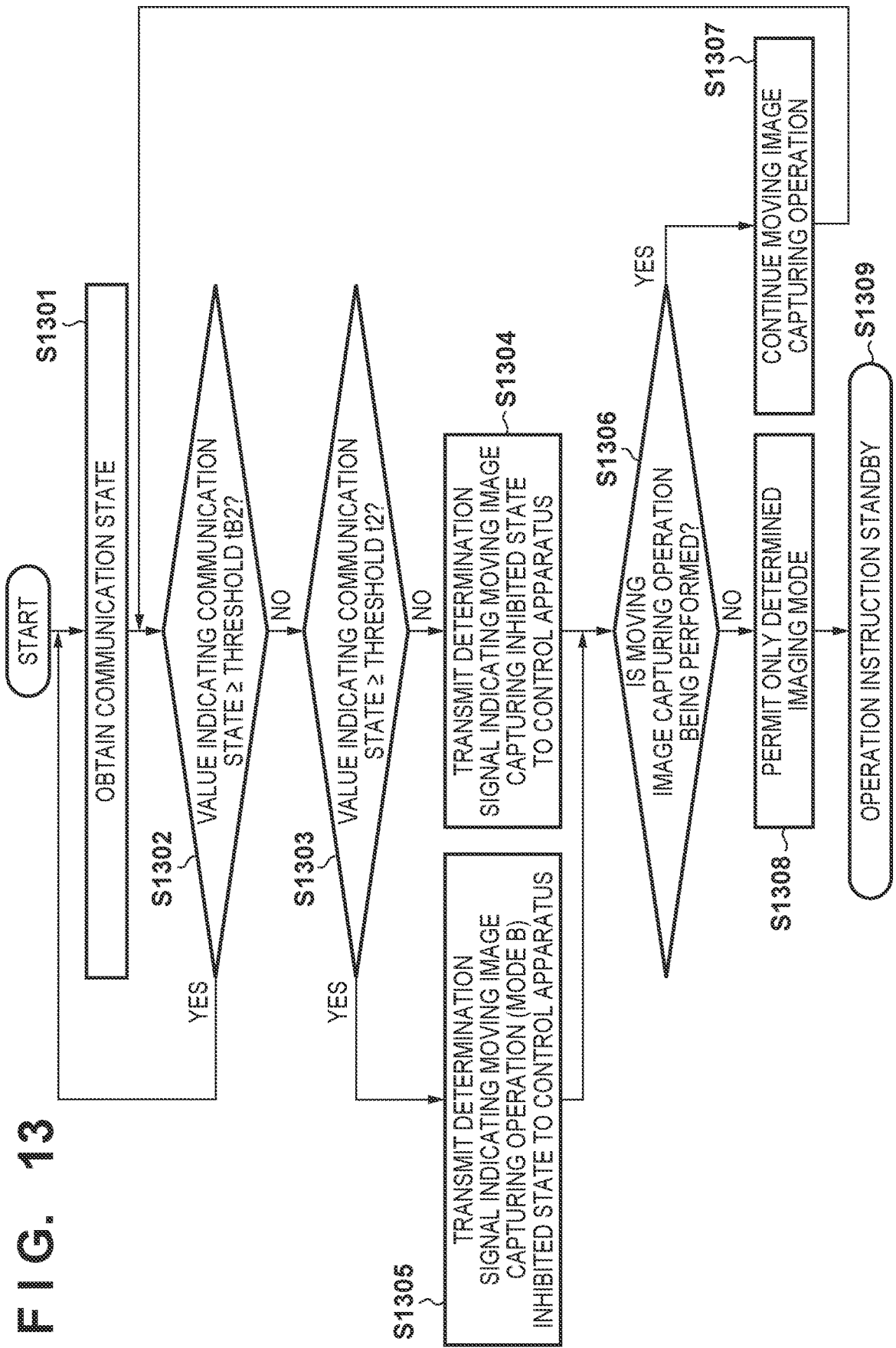

CONTROL APPARATUS, CONTROL SYSTEM, CONTROL METHOD, MEDICAL IMAGING APPARATUS, MEDICAL IMAGING SYSTEM, AND IMAGING CONTROL METHOD FOR SWITCHING IMAGING MODES BASED ON COMMUNICATION STATE

BACKGROUND OF THE INVENTION

Field of the Invention

The present invention relates to a control apparatus, a control system, a control method, a medical imaging apparatus, a medical imaging system, and an imaging control method.

Description of the Related Art

A radiation imaging system that uses a radiation sensor is widely used in industrial and medical fields. For example, Japanese Patent Laid-Open No. 2009-272673 discloses a radiation imaging system that can perform imaging by a plurality of imaging modes according to the purpose, such as a moving image capturing operation and a still image capturing operation. A radiation imaging apparatus, a control apparatus, and a radiation generating apparatus that irradiates an object with radiation from the radiation imaging system and are connected to each other via a connection interface. As arrangements for connecting the apparatuses, there are, for example, a wired-connection arrangement using a general purpose UTP (Unshielded Twist Pair) cable or the like and a wireless-connection arrangement connecting through a wireless interface. For example, Japanese Patent Laid-Open No. 2011-41866 discloses an example of the arrangement of a radiation imaging system that connects through a wireless interface such as a wireless LAN typified by IEEE802.11.

The wireless communication state constantly changes due to the distance or an obstacle between communicating devices, or radio interference from other wireless devices. The wireless communication stability and communication throughput change from the changes in the wireless communication state. Due to such characteristics of wireless communication, problems easily occur in the radiation imaging system connected by a wireless interface. For example, a user may not be able to implement a desired imaging operation particularly in a moving image capturing operation that requires higher communication throughput than a still image capturing operation. Japanese Patent No. 04519131 discloses an arrangement in which one threshold is provided for the wireless communication state, the device operation state is divided into two states based on the result of comparison with the threshold, and the executable operation mode is restricted if a value indicating the communication state is smaller than the threshold.

For example, when there are imaging modes, such as the still image capturing operation and the moving image capturing operation, each having a different communication target image data amount, a communication state may not be suitable for one imaging mode even if it is the communication state suitable for another imaging mode. For example, when a moving image capturing operation is to be performed in a situation where a still image capturing operation was performed under a predetermined communication state, if the communication state is not suited for the moving image capturing operation, an appropriate moving image capturing operation may not be performed even when the imaging mode is switched to the moving image capturing operation.

The present invention provides a technique for performing appropriate imaging in a switched imaging mode.

SUMMARY OF THE INVENTION

According to one aspect of the present invention, there is provided a control apparatus that controls medical imaging, comprising: a communication unit configured to communicate with an imaging unit via a communication path that includes a wireless channel; an imaging control unit configured to cause the imaging unit to execute a plurality of imaging modes including a first imaging mode and a second imaging mode which obtains a larger data amount from imaging than the first imaging mode; a restricting unit configured to restrict transition of the imaging mode when a value indicating the state of communication with the imaging unit by the communication unit is smaller than a threshold; and a setting unit configured to set different threshold values for a case in which the first imaging mode transits to the second imaging mode and a case in which the second imaging mode transits to the first imaging mode.

According to another aspect of the present invention, there is provided a medical imaging apparatus that outputs, via a wireless communication unit, image data generated based on a detection result of a detection unit, comprising: an obtaining unit configured to obtain a communication state of the wireless communication unit; and a control unit configured to control the detection unit based on a result of a comparison between the communication state and one of a first threshold obtained by adding a variation range of the communication state to a communication rate necessary for a moving image capturing operation and a second threshold corresponding to the communication rate.

The present invention can provide a technique for performing appropriate imaging in a switched imaging mode.

Further features of the present invention will become apparent from the following description of exemplary embodiments (with reference to the attached drawings).

BRIEF DESCRIPTION OF THE DRAWINGS

FIGS. 5A and 5B are views each showing an example of a display unit screen according to the first embodiment;

FIG. 7 is a view showing an example of a lookup table according to the first embodiment;

FIG. 10 is a view exemplifying the relationships between thresholds according to the second embodiment;

FIG. 11 is a flowchart showing an operation example of a medical imaging apparatus according to the second embodiment;

FIG. 13 is a flowchart showing the operation example of the medical imaging apparatus according to the second embodiment;

DESCRIPTION OF THE EMBODIMENTS

Embodiments of the present invention will be exemplarily described in detail below with reference to the accompanying drawings. Note that components to be described in these embodiments are merely examples. The technical scope of the present invention is defined by the scope of the claims, and is not limited by the following embodiments.

First Embodiment

Figure 1:
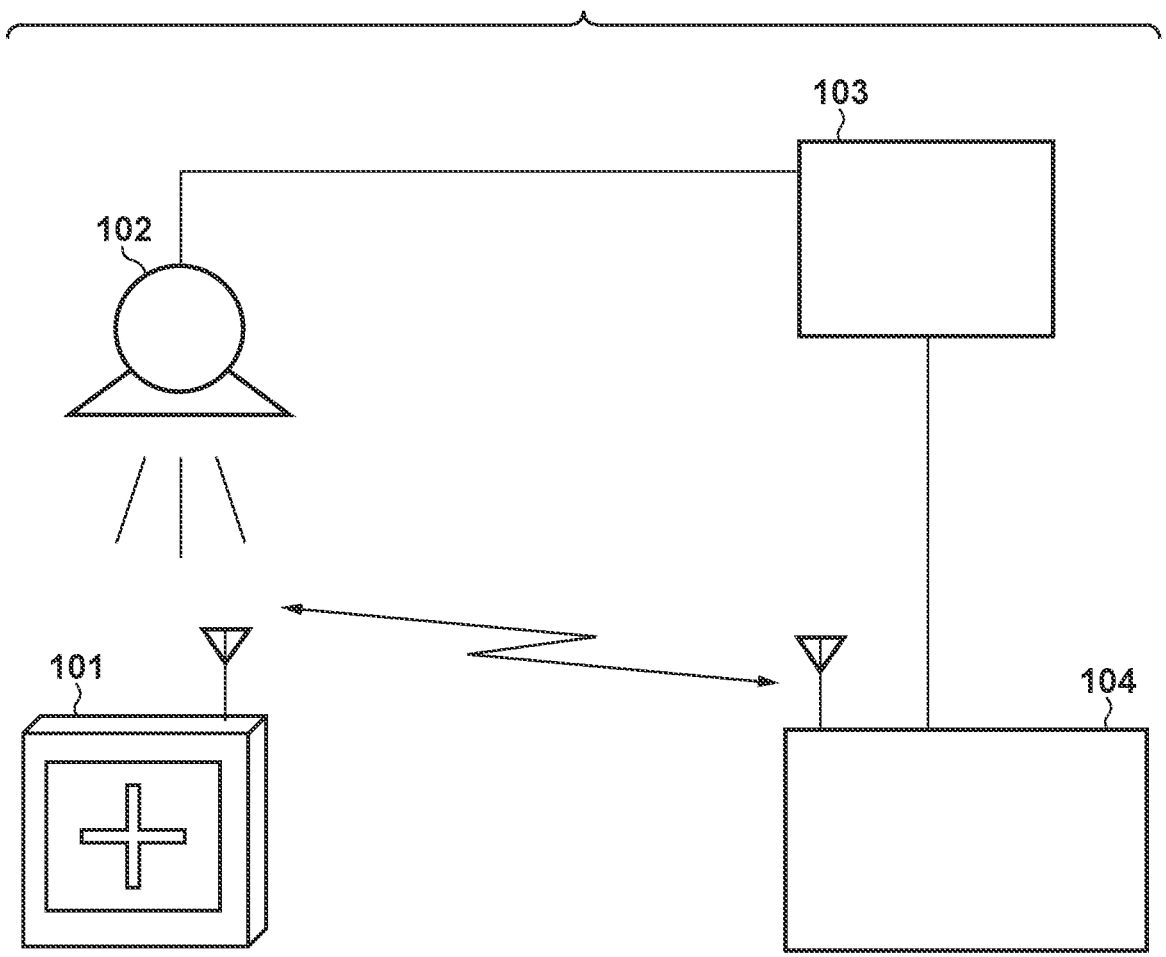
FIG. 1 is a view showing an example of the arrangement of a medical imaging system according to an embodiment.

FIG. 1 is a view showing an example of the arrangement of a medical imaging system according to the first embodiment. The medical imaging system includes a medical imaging apparatus, a radiation generating apparatus, and a processing apparatus (control apparatus) that controls the operation state of the medical imaging apparatus and processes image data. The medical imaging apparatus can output, via a wireless communication unit, image data generated based on the detection result of a detection unit (for example, image data generated by detecting radiation with the detection unit).

The arrangement of the first embodiment is applicable, as a medical imaging apparatus, to an ultrasonic imaging apparatus which includes, for example, a hand-held probe and wirelessly transmits an image signal to a control apparatus or a medical imaging apparatus such as an ophthalmic imaging apparatus or the like. The arrangement of this embodiment is also applicable, as a medical imaging apparatus, to a radiation imaging apparatus which performs radiation imaging by using X-rays, α-rays, β-rays, γ-rays, or a particle beam.

An arrangement including a medical imaging apparatus (radiation imaging apparatus 101), a radiation generating apparatus (radiation tube 102, radiation generating apparatus 103), and a processing apparatus (control apparatus 104) as a medical imaging system will be described below. Note that the overall arrangement of the medical imaging system (radiation imaging system) may sometimes be called the medical imaging apparatus (radiation imaging apparatus).

Figure 14:
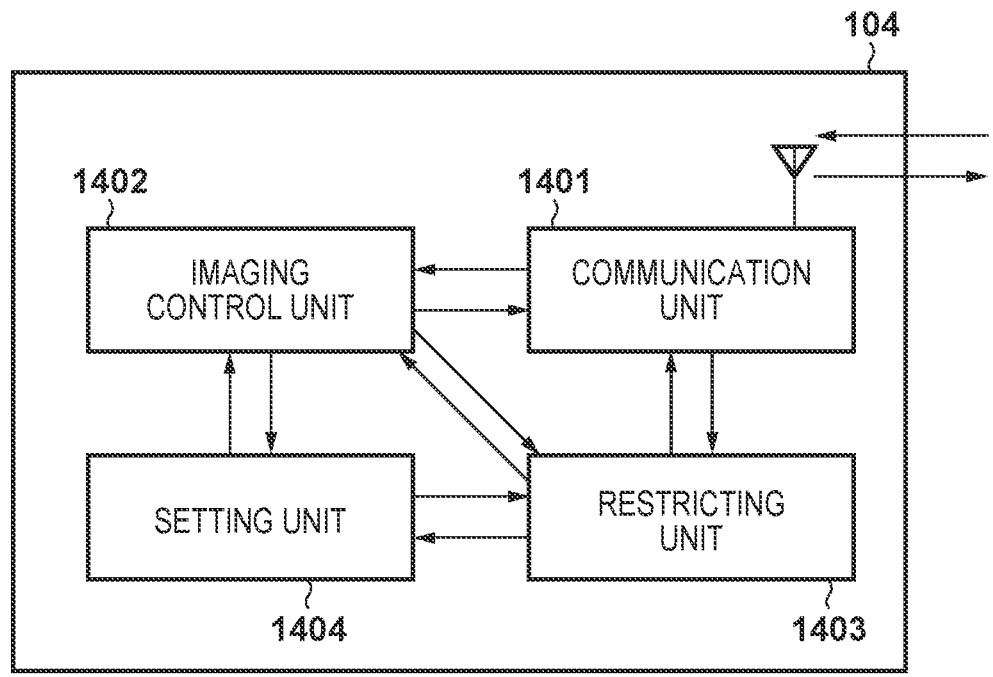
FIG. 14 is a block diagram showing the arrangement example of a control unit according to the embodiment.

FIG. 14 is a block diagram for explaining the arrangement of the control apparatus 104. The control apparatus 104 performs control of medical imaging in the medical imaging apparatus. The control unit 104 includes, as shown in FIG. 14, a communication unit 1401, an imaging control unit 1402, a restricting unit 1403, and a setting unit 1404.

The communication unit 1401 has a wireless communication module and can communicate with, for example, the imaging unit of the medical imaging apparatus (radiation imaging apparatus) via a communication path that includes a wireless channel. For example, a wireless communication module capable of communicating with the communication unit 1401 of the control apparatus 104 is installed in the imaging unit of the medical imaging apparatus (radiation imaging apparatus) and the apparatuses can communicate with each other via the respective wireless communication modules. Alternatively, an external wireless module that connects by wire can be connected to the imaging unit of the medical imaging apparatus (radiation generating apparatus) and the communication unit 1401 of the control apparatus 104 can communicate with the imaging unit of the medical imaging apparatus (radiation imaging apparatus) via the external wireless module.

The imaging control unit 1402 can cause the imaging unit to execute a plurality of imaging modes including a first imaging mode and second imaging modes that can obtain a larger data amount from imaging than the first imaging mode. The restricting unit 1403 restricts the transition of the imaging mode when a value indicating the communication state of the communication unit 1401 with the imaging unit is smaller than a threshold. On the other hand, when the value indicating the communication state is larger than the threshold (equal to or larger than the threshold), the restricting unit 1403 determines that the communication state is good and permits the transition of the imaging mode.

Figure 15:
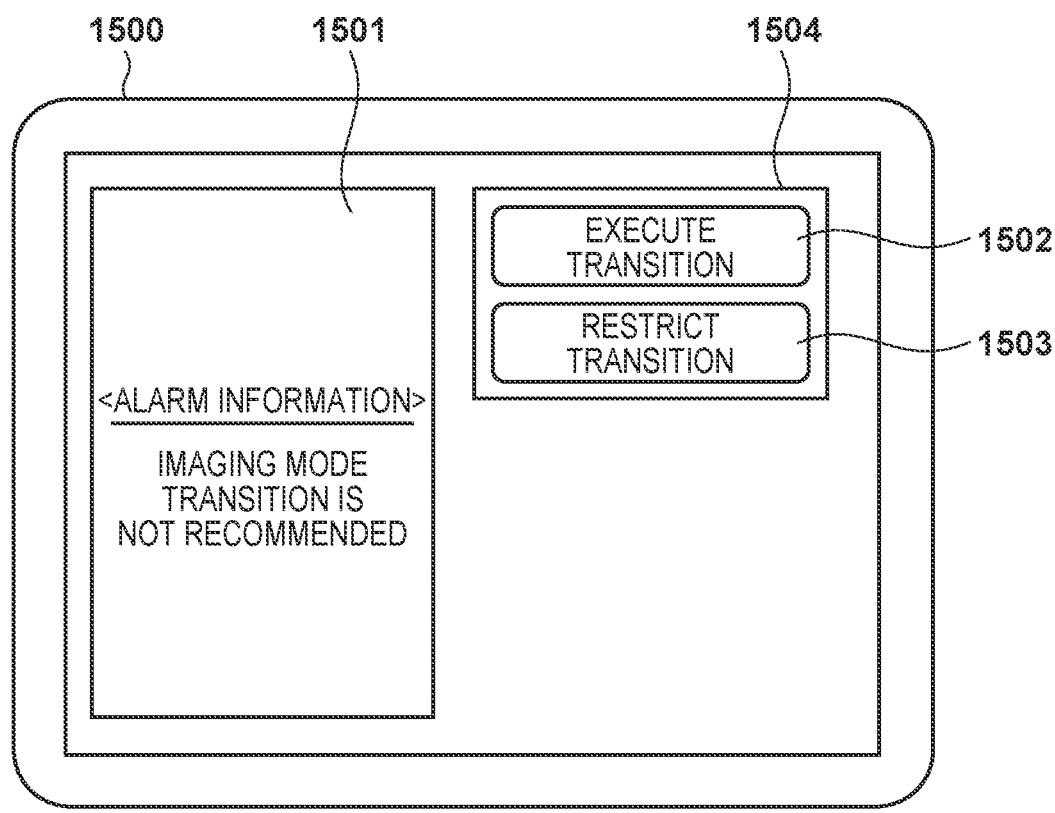
FIG. 15 is a view showing an example of a display unit screen of the control unit.

FIG. 15 is a view showing an example of the screen of a display unit 1500 in the control apparatus 104. The restricting unit 1403 causes the display unit to display alarm information 1501 about the restriction of imaging mode transition (that imaging mode transition is not recommended) and an operation input unit 1504 for accepting an operation input by a user. An operation input unit 1502 (execute transition) for accepting operation input for transition execution and an operation input unit 1503 (restrict transition) for accepting operation input for transition restriction are displayed on the operation input unit 1504.

When the value indicating the communication state is smaller than the threshold, the restricting unit 1403 restricts imaging mode transition. In this case, the restricting unit 1403 causes the display unit 1500 to display the alarm information 1501 about the restriction of imaging mode transition (that imaging mode transition is not recommended). If operation by the user is input via the operation input unit 1502 (execute transition) while the alarm information 1501 is displayed on the display unit, the restricting unit 1403 executes imaging mode transition in accordance with the user operation even when the value indicating the communication state is smaller than the threshold. On the other hand, if operation by the user is input via the operation input unit 1503 (restrict transition), the restricting unit 1403 restricts the imaging mode transition in accordance with the user operation.

Returning to the explanation of FIG. 14, assume that the setting unit 1404 sets different threshold values for a case in which the first imaging mode transits to the second imaging modes and for a case in which the second imaging modes transit to the first imaging mode. For example, a still image capturing mode is included as the first imaging mode. The second imaging modes include modes such as a moving image capturing mode, tomography mode such as tomosynthesis, and long-length imaging in which a long-length image is acquired by obtaining a plurality of radiation images by simultaneously irradiating a plurality of FPDs with radiation in a state where the plurality of FPDs are aligned and combining the obtained radiation images. The setting unit 1404 sets, for example, the threshold for a case in which the still image capturing mode transits to the moving image capturing mode to have a larger value than the threshold for a case in which the moving image capturing mode transits to the still image capturing mode.

When setting a threshold, the setting unit 1404 can set the threshold according to the operation input by the user. In addition, the magnitude of threshold can be changed depending on the type (for example, the above-described moving image capturing mode, tomography mode, long-length imaging mode, or the like) of the second imaging mode. For example, assume that "settings" include a case in which the magnitudes of thresholds for the moving image capturing mode and the still image capturing mode are encoded on a program and the setting unit 1404 loads the encoded thresholds.

The imaging control unit 1402 can cause the imaging unit of the medical imaging apparatus (radiation imaging apparatus) to execute imaging by the plurality of second imaging modes that can obtain a larger data amount from imaging than the first imaging mode. The setting unit 1404 can set different threshold values for at least two imaging modes out of the plurality of second imaging modes. When there are a plurality of imaging types of the second imaging modes, the setting unit 1404 can set different thresholds for the respective imaging operations corresponding to the second imaging modes. In addition, the setting unit 1404 can set a threshold according to the operation input of the user. Further, the setting unit 1404 can set different thresholds for the respective imaging operations corresponding to the second imaging modes by loading a program in which the magnitudes of the thresholds have been set. When there are a plurality of imaging types of the second imaging modes, the setting unit 1404 can change the threshold value in accordance with the data amount of each image output from the imaging unit per unit time. The setting unit 1404 can, for example, set the threshold larger for an imaging (tomosynthesis) operation of a large data amount than for fluoroscopic imaging. From this arrangement, an appropriate threshold can be set in accordance with the data amount of the image output from the imaging unit on an imaging mode or unit time basis.

The data amount of the image output from the imaging unit for each unit of time and the data amount of the image generated by the imaging unit per each unit of time can be different concepts. For example, the imaging unit of the medical imaging apparatus (radiation imaging apparatus) may not output all the generated data in real-time, but instead the imaging unit may accumulate and transmit (output) some of the generated data. When the imaging unit accumulates and transmits (outputs) some of the generated data, for example, as data to be transmitted during imaging in the moving image capturing operation, ¼ of the generated data is transmitted as reduced data. When the imaging unit controls the transmission of the generated data so that the remaining ¾ of the data is transmitted after imaging, the image data amount output from the imaging unit per unit time and the image data amount generated by the imaging unit per unit time become different. Note that the ratio of data transmitted (output) while being partially accumulated is only exemplary and the arrangement of this embodiment is not limited to this example.

Although the arrangement of the control apparatus 104 has been described as a single apparatus in FIG. 14, it is not limited to a single apparatus arrangement. For example, the arrangement shown in FIG. 14 can be implemented by a plurality of mutually communicating apparatuses. A system (control system) configured from a plurality of mutually communicating apparatuses includes the communication unit 1401, the imaging control unit 1402, the restricting unit 1403, and the setting unit 1404 and can implement the same functions as the control apparatus 104 even in the control system configured from a plurality of apparatuses.

Figure 16:
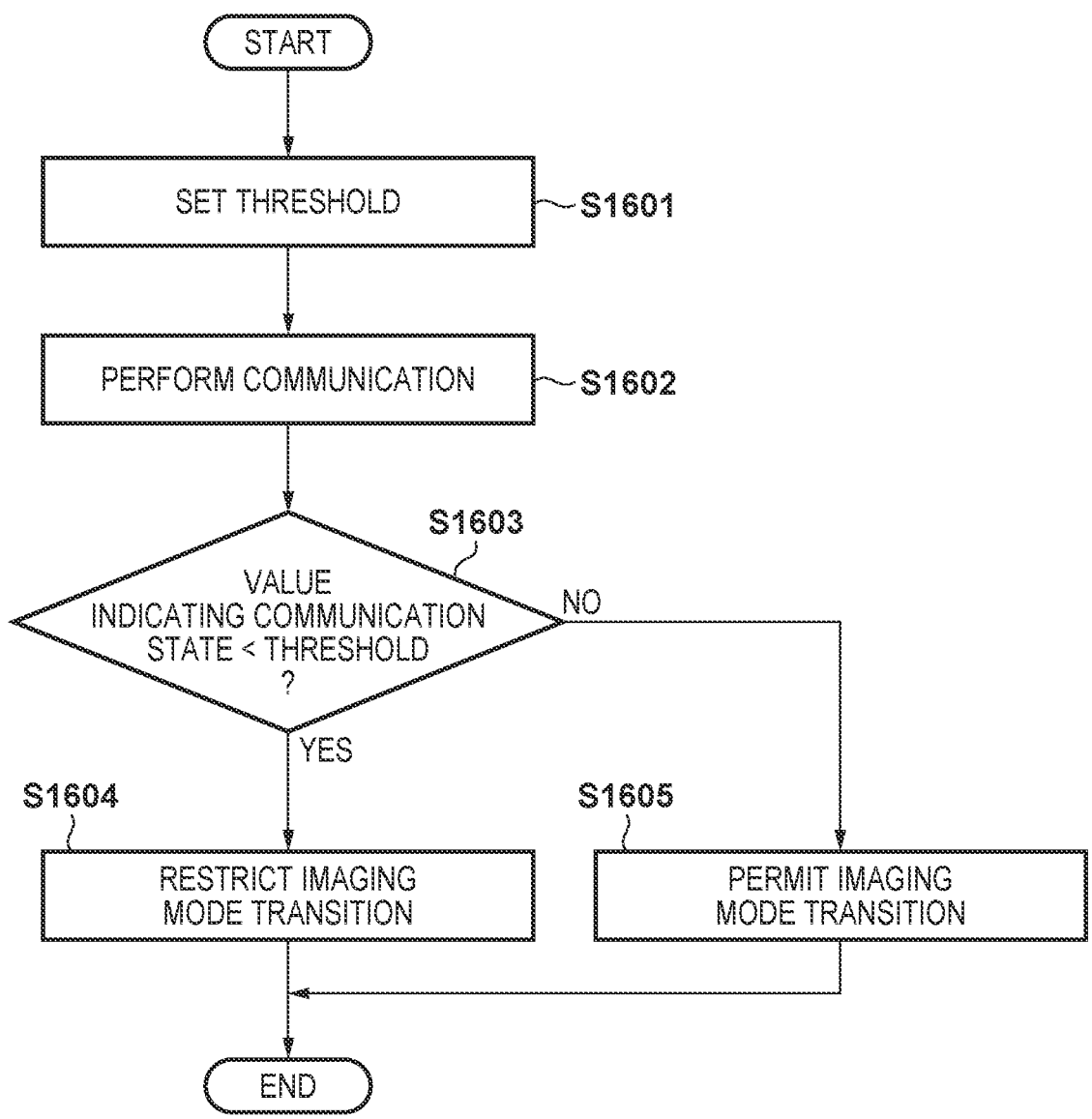
FIG. 16 is a flowchart for explaining the control method of the control apparatus.

FIG. 16 is a flowchart for explaining the control method of the control apparatus for controlling medical imaging. In step S1601, the setting unit 1404 sets different magnitudes of threshold values for a case in which the first imaging mode transits to the second imaging modes and for a case in which the second imaging modes transit to the first imaging mode.

In step S1602, the communication unit 1401 communicates with the imaging unit of the medical imaging apparatus (radiation imaging apparatus) via the communication path that includes the wireless channel.

In step S1603, the restricting unit 1403 compares the value indicating the communication state with the threshold. If the value indicating the communication state with the imaging unit by the communication unit 1401 is smaller than the threshold (YES in step S1603), the restricting unit 1403 restricts the imaging mode transition (step S1604). On the other hand, in step S1603, if the value indicating the communication state is larger than the threshold (equal to or larger than the threshold) (NO in step S1603), the restricting unit 1403 causes the process to advance to step S1605. Then, in step S1605, the restricting unit 1403 determines that the communication state is good and permits the imaging mode transition and ends the process.

According to the arrangement of the control apparatus 104 different magnitudes of the threshold values can be set for a case in which the first imaging mode transits to the second imaging modes that can obtain a larger data amount from imaging than the first imaging mode and for a case in which the second imaging modes transit to the first imaging mode. Based on the thresholds set to have different values, imaging mode transition can be restricted when the value indicating the communication state with the imaging unit is smaller than the threshold.

The radiation imaging apparatus 101 incorporates a wireless transmission/reception apparatus (wireless communication unit) and can wirelessly communicate with the wireless transmission/reception apparatus (wireless communication unit) of another apparatus. In FIG. 1, a wireless transmission/reception apparatus (wireless communication unit) is also provided in the control apparatus 104 and the control apparatus 104 and the radiation imaging apparatus 101 can wirelessly communicate via their respective wireless transmission/reception apparatuses (wireless communication units).

The radiation imaging apparatus 101 can also perform the still image capturing operation and the moving image capturing operation by a plurality of types of modes and can perform imaging in accordance with instructions from the control apparatus 104. The radiation tube 102 and the radiation generating apparatus 103 generate radiation and perform irradiation. At the time of radiation imaging, the radiation tube 102 is installed relative to the radiation imaging apparatus 101. Generally, a personal computer (information processing apparatus) is used for the control apparatus 104. The control apparatus 104 incorporates a wireless transmission/reception apparatus (wireless communication unit), performs wireless communication with the radiation imaging apparatus 101, and can transmit and receive information. The control apparatus 104 is also provided with a display device and an input interface such as a touch panel, a mouse, or a keyboard. The control apparatus 104 can use these input interface and display device to instruct the operation of radiation imaging apparatus 101, or perform image processing, saving, or display upon reception of a radiation image.

The control apparatus 104 can also connect with the radiation generating apparatus 103, obtain information of the radiation generating apparatus 103, and relay and transmit synchronization signals from the radiation generating apparatus 103 to the radiation imaging apparatus 101. Although FIG. 1 exemplifies an arrangement in which the radiation imaging apparatus 101 and the control apparatus 104 respectively incorporate the wireless transmission/reception apparatus, it also can be an arrangement in which a wireless access point that functions as the wireless transmission/reception apparatus (wireless communication unit) is included in the communication path. For example, it may be an arrangement in which the control apparatus 104 does not incorporate wireless transmission/reception apparatus and the radiation imaging apparatus 101 and the wireless access point performs wireless communication or an arrangement in which the wireless access point and the control apparatus 104 are connected by wire. The radiation generating apparatus 103 can also incorporate a wireless transmission/reception apparatus (wireless communication unit) and perform wireless communication.

Figure 2:
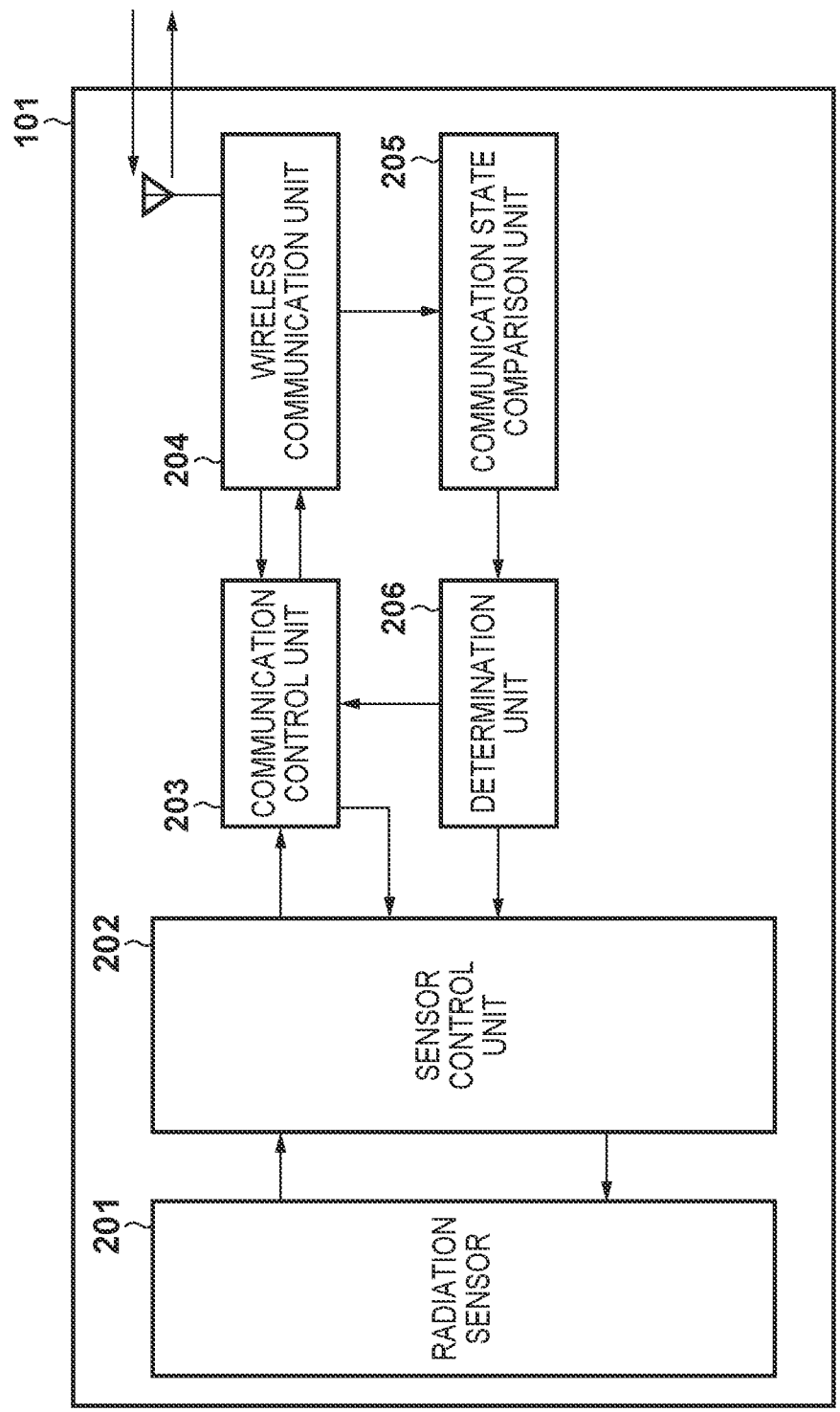
FIG. 2 is a block diagram showing an example of the arrangement of a medical imaging apparatus according to the embodiment.

FIG. 2 is a view showing an example of the arrangement of the radiation imaging apparatus 101 according to the first embodiment. The radiation imaging apparatus 101 outputs, via the wireless communication unit, image data generated from detecting radiation that passed through an object. The radiation imaging apparatus 101 includes a radiation sensor 201, a sensor control unit 202, a communication control unit 203, a wireless communication unit 204, a communication state comparison unit 205, and a determination unit 206. The radiation sensor 201 receives and changes the radiation that has passed through the object into digital data and outputs the digital data. The sensor control unit 202 drives the radiation sensor 201 in the set operation mode (still image capturing mode or moving image capturing mode), reads out the output digital data, and generates image data. The communication control unit 203 controls communication with another apparatus and performs communication control to transmit information to the transmission destination. The wireless communication unit 204 functions as an interface for wireless communication with the wireless transmission/reception apparatus (wireless communication unit) of another apparatus. The communication state comparison unit 205 obtains status information indicating the wireless communication state obtained by the wireless communication unit 204 at the time of wireless communication and compares the information with a predetermined threshold. The determination unit 206 determines the operation mode to be permitted for the current wireless communication state based on the comparison result of the communication state comparison unit 205 and outputs the determination result to the sensor control unit 202 and the communication control unit 203. The sensor control unit 202 controls the radiation sensor based on a result of a comparison between the communication state and a first threshold (for example, t1 shown in FIG. 3) obtained by adding a variation range of the communication state to the communication rate necessary for the moving image capturing operation or a second threshold (for example, t2 shown in FIG. 3) corresponding to the communication rate.

When the moving image capturing operation is to be executed by the radiation sensor 201 (detection unit), the sensor control unit 202 can change the frame rate of the moving image capturing operation based on the imaging conditions. The sensor control unit 202 can also change (reduce) the image size by thinning out, on a pixel basis, an image output from the radiation sensor 201 or by averaging and combining the pixel values of a plurality of pixels into one pixel. Selectable combinations of image size change by thinning out on a pixel basis or combining pixels are predetermined in the radiation imaging system, and the user can set desired imaging conditions out of the options through the control apparatus 104. The imaging conditions selected by the user are input to the sensor control unit 202 via the wireless communication unit 204 and the communication control unit 203. The sensor control unit 202 can control the radiation sensor 201 based on the input imaging conditions.

Figure 3:
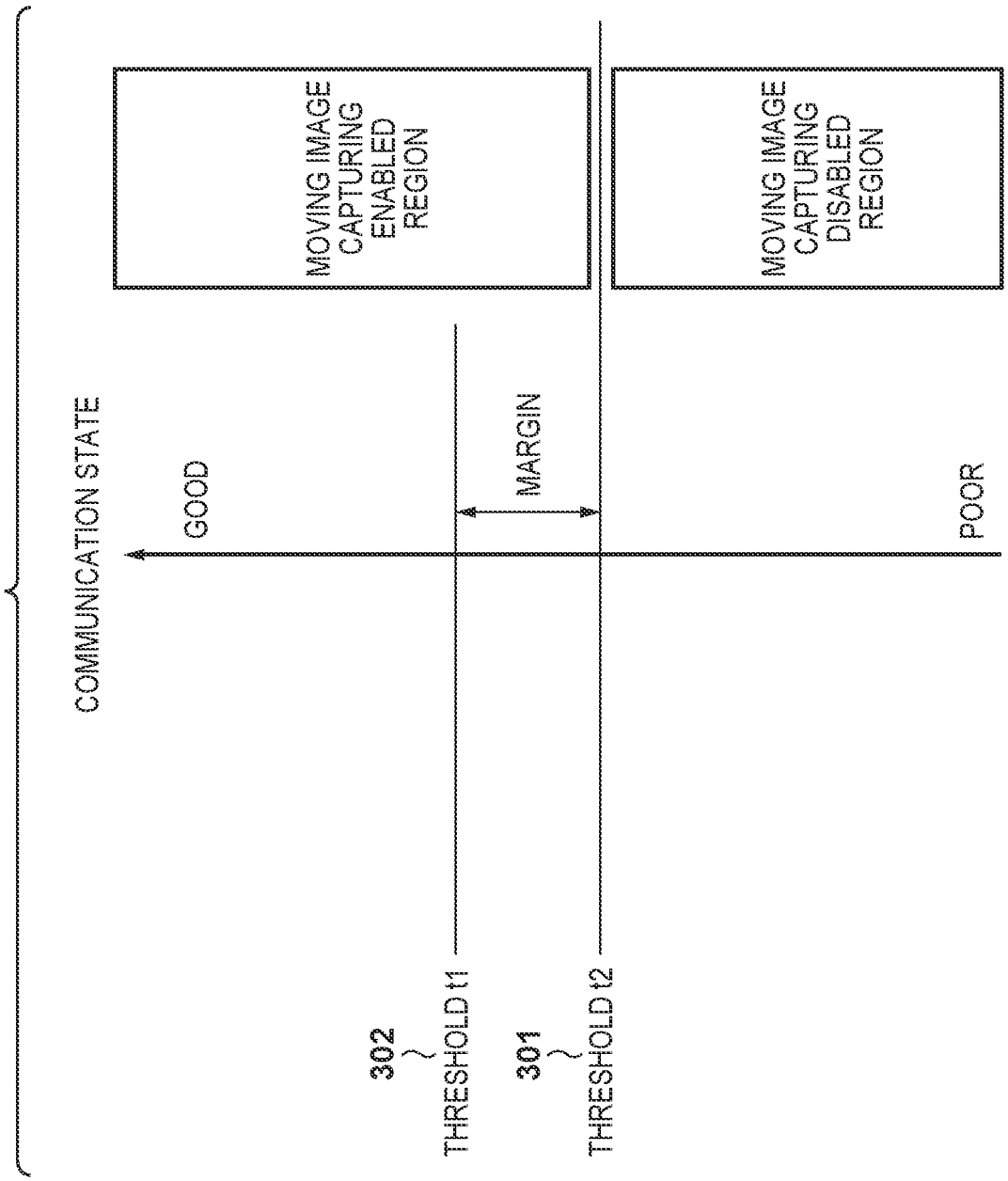
FIG. 3 is a view exemplifying the relationships between thresholds according to the first embodiment.

FIG. 3 is a view exemplifying the relationships of the plurality of thresholds used for imaging control of the radiation imaging apparatus of this embodiment. Comparison processing by the communication state comparison unit 205 of this embodiment will be described with reference to FIG. 3. The communication state comparison unit 205 compares the status information indicating the wireless communication state obtained by the wireless communication unit 204 at the time of wireless communication with a predetermined threshold. In the moving image capturing operation, the necessary wireless communication rate is determined mainly by the image size (number of pixels) and frame rate settings. The necessary wireless communication rate increases depending on the increase in the image size or the frame rate. The wireless communication rate and the information indicating a good wireless communication state (status information indicating the wireless communication state) generally have a relationship of monotonic increase. Assume that a threshold t2 301 is the communication state threshold corresponding to the minimum wireless communication rate necessary for the moving image capturing operation of the radiation imaging system.

Assume also that a threshold t1 302 is the communication state threshold obtained by adding a predetermined margin to the threshold t2 301. The margin corresponds to the predictable variation range of the communication state. The communication state comparison unit 205 can use this margin as a common fixed value regardless of the installation environment. The communication state comparison unit 205 can also premeasure the variation of the communication state for each installation environment before installing the radiation imaging apparatus and set the margin based on the measurement result. The communication state comparison unit 205 can also set a fixed initial value and continue to accumulate data by measuring the communication state in its installation environment after installation to calculate and use an appropriate margin for the installation environment of the apparatus. Note that the relative relationship between the threshold t1 302 and the threshold t2 301 is threshold t1>threshold t2. The radiation imaging apparatus can capture a moving image when the value indicating the communication state becomes equal to or larger than the threshold t2 301. The still image capturing operation is also possible when the value indicating the communication state is equal to or larger than the threshold t2 301. When the value indicating the communication state becomes smaller than the threshold t2 301, the radiation imaging apparatus 101 cannot perform the moving image capturing operation and can perform only the still image capturing operation.

Figure 4:
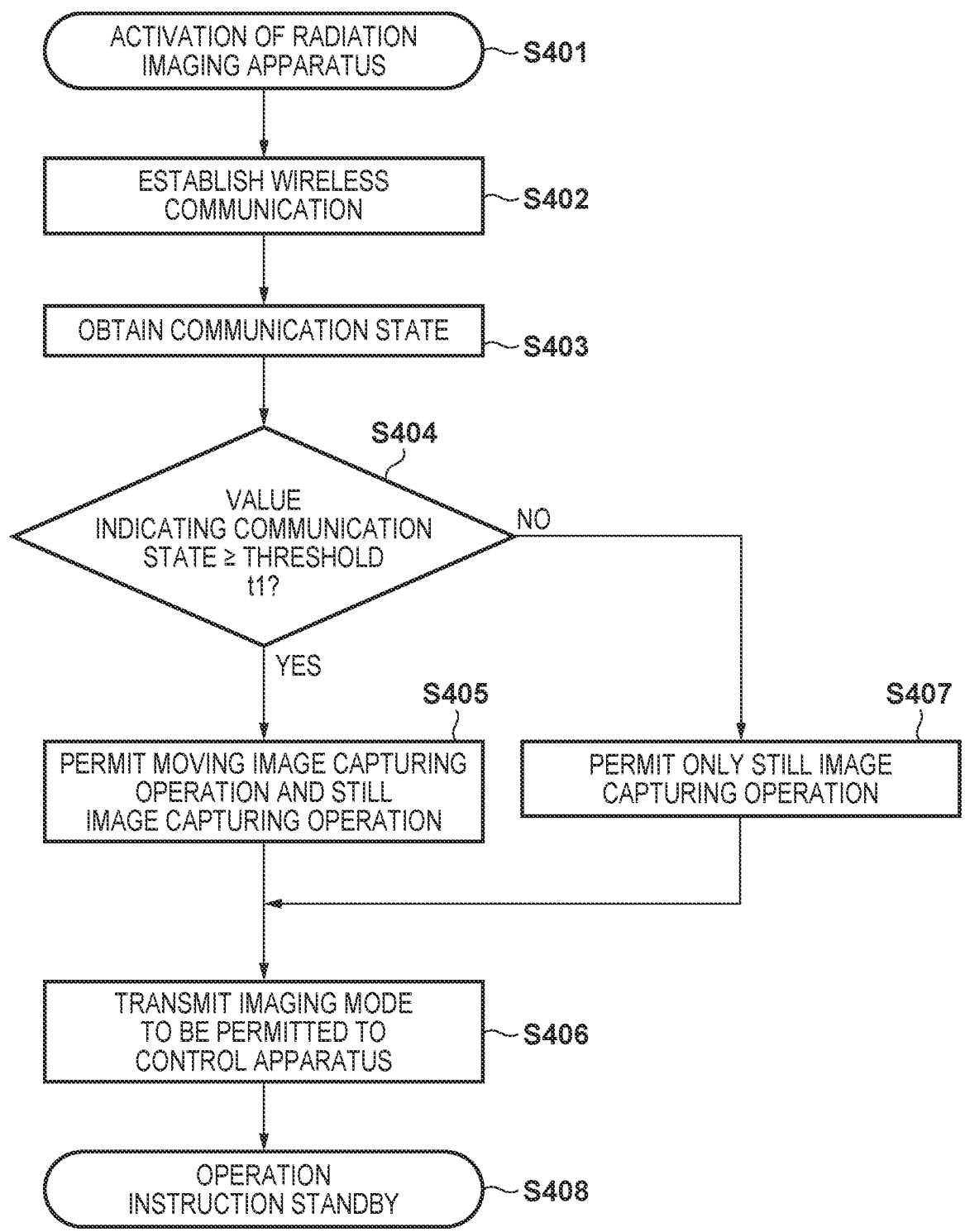
FIG. 4 is a flowchart showing an operation example of a medical imaging apparatus according to the first embodiment.

FIG. 4 is a flowchart showing an example of the operation of the radiation imaging apparatus according to the first embodiment. FIG. 4 shows the operation immediately after activation (at the time of activation) of the radiation imaging apparatus 101. The radiation imaging apparatus 101 is activated in step S401. In step S402, the communication control unit 203 of the radiation imaging apparatus 101 controls the wireless communication unit 204 and establishes wireless communication with a preset connection destination. Assume that the connection destination is the control apparatus 104. If connection is not possible with the preset connection destination, the communication control unit 203 of the radiation imaging apparatus 101 performs display control to cause the display unit to display a message indicating that no communication can be established and notifies the user of it. Assume that the radiation imaging apparatus 101 includes an LED or a small display device as a display unit arrangement. Based on the determination signal of the determination unit 206, the display unit can display the operation mode that is to be permitted for the current wireless communication state (for example, a state in which the moving image capturing operation and the still image capturing operation are permitted or a state in which only the still image capturing operation is permitted).

After communication is established, in step S403, the communication state comparison unit 205 of the radiation imaging apparatus 101 obtains, as communication state obtainment processing, the status information indicating the wireless communication state from the wireless communication unit 204. In step S404, the communication state comparison unit 205 compares the obtained value indicating the communication state (status information indicating the wireless communication state) with the threshold t1. The determination unit 206 determines the operation mode to be permitted for the current wireless communication state based on the comparison result of the communication state comparison unit 205. If the communication state (status information indicating the wireless communication state) from the comparison result of the communication state comparison unit 205 has a value equal to or larger than the threshold t1 (equal to or larger than the threshold) (YES in step S404), the process advances to step S405.

In step S405, the determination unit 206 determines the operation mode to be permitted for the current wireless communication state based on the comparison result of the communication state comparison unit 205. If the value indicating the communication state is equal to or larger than the threshold t1, the determination unit 206 permits the moving image capturing operation and the still image capturing operation as the operation modes to be permitted for the current wireless communication state. A determination signal indicating the determination result of the determination unit 206 is transmitted from the determination unit 206 to the sensor control unit 202 and it becomes a state in which the moving image capturing operation and the still image capturing operation are permitted.

In step S406, the determination unit 206 outputs the determination signal indicating the determination result to the communication control unit 203. The communication control unit 203 controls the wireless communication unit 204 so that the determination signal from the determination unit 206 is transmitted to the control apparatus 104. Based on the determination signal, the control apparatus 104 sets the still image capturing mode and the moving image capturing mode as the operation modes to be permitted for the current wireless communication state.

On the other hand, if the communication state (status information indicating the wireless communication state) from the comparison result of the communication state comparison unit 205 in step S404 has a value smaller than the threshold t1 (less than the threshold) (NO in step S404), the process advances to step S407.

In step S407, the determination unit 206 determines the operation mode to be permitted for the current wireless communication state based on the comparison result of the communication state comparison unit 205. If the value indicating the communication state is smaller than the threshold t1, the determination unit 206 inhibits the moving image capturing operation and permits only the still image capturing operation as the operation mode to be permitted for the current wireless communication state. The determination signal indicating the determination result of the determination unit 206 is transmitted from the determination unit 206 to the sensor control unit 202 and it becomes a state in which the still image capturing operation is permitted.

In step S406, the determination unit 206 outputs the determination signal indicating the determination result to the communication control unit 203. The communication control unit 203 controls the wireless communication unit 204 so that the determination signal from the determination unit 206 is transmitted to the control apparatus 104. Based on the determination signal, the control apparatus 104 sets the still image capturing mode as the operation mode to be permitted for the current wireless communication state. In step S408, the radiation imaging apparatus 101 changes to a standby state to wait for an operation instruction from the control apparatus 104.

As the communication state (status information indicating the wireless communication state), the connection destination wireless intensity (reception intensity, hereinafter) receivable by the wireless communication unit 204 can be continuously obtained for a predetermined time and its average value or the minimum value can be used as the communication state. The communication rate or the error rate calculated from transmitting test data to the connection destination can be also used. A combination of these can be also used. Additionally, during the moving image capturing operation, the communication rate or the error rate can be obtained by transferring the actual moving image data. Since the communication state changes instantaneously, the value indicating the communication state (status information indicating the wireless communication state) may temporarily fall below the threshold t1 to an extent which has no actual influence on the transfer of the moving image. In order to prevent the influence of the instantaneous changes of the communication state, the communication state comparison unit 205 can perform techniques, such as averaging processing and low-pass filter, which remove such an influence during the communication state obtainment processing.

Processing of the control apparatus 104 upon reception of the determination signal will be described next. Based on the determination signal received from the radiation imaging apparatus 101, the control apparatus 104 displays the operation mode of the radiation imaging apparatus 101 on a display unit 501 so that it may be understood by the user. FIGS. 5A and 5B are views each showing an example of the display screen of the control apparatus 104. The control apparatus 104 displays a console screen 502 for controlling the radiation imaging apparatus 101 on the display unit 501. FIG. 5A shows a state in which the moving image capturing operation and the still image capturing operation are permitted as the operation mode of the radiation imaging apparatus 101. Imaging mode selection buttons 503 are selection units for selecting the imaging mode, and the user can select, out of the moving image capturing operation and the still image capturing operation, one imaging mode via the imaging mode selection buttons 503. FIG. 5B shows a state in which only the still image capturing operation has been permitted as the operation mode of the radiation imaging apparatus 101. In FIG. 5B, only the imaging mode of the still image capturing operation can be selected in imaging mode selection buttons 504. The selection button for the moving image capturing operation has been grayed out and cannot be selected in the imaging mode selection buttons 504.

When the user selects the imaging mode selection buttons, the processing advances to the imaging sequences corresponding to the respective imaging modes. If the user selects the moving image capturing operation, the control apparatus 104 selects the frame rate, the image size, irradiation conditions, and the like in accordance with the selection operation. Based on the selected imaging conditions, the radiation tube 102 and the radiation generating apparatus 103 generate radiation and perform irradiation, and the radiation imaging apparatus 101 starts imaging. In the moving image capturing operation, pulse imaging in which images are obtained in accordance with the pulses of radiation irradiating the object and continuous imaging in which the object is continuously irradiated with radiation can be executed. If the user selects the still image capturing operation, the control apparatus 104 selects the irradiation conditions, an imaging region, and the like in accordance with the user selection operation, and the radiation imaging apparatus 101 starts imaging.

Figure 6:
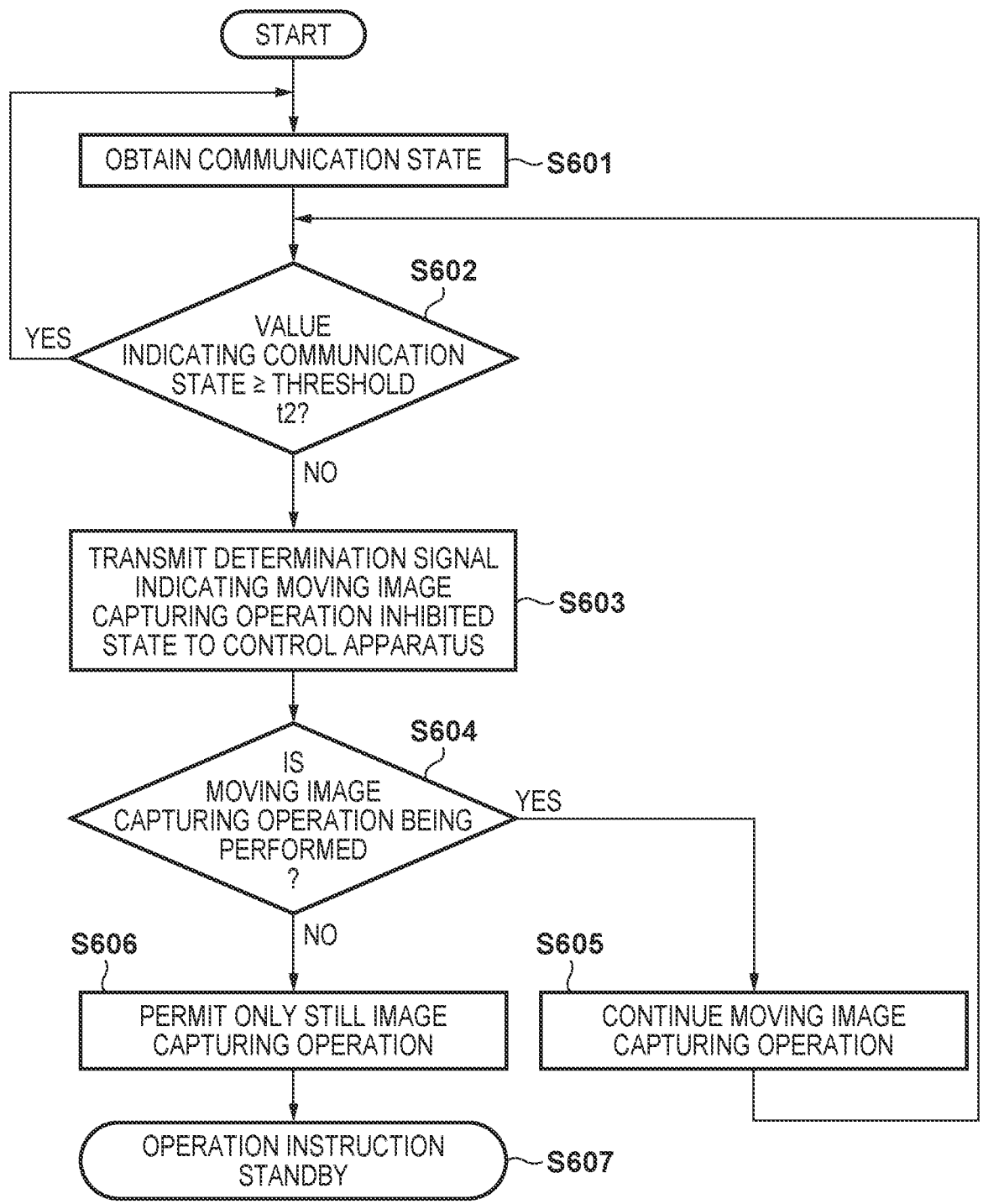
FIG. 6 is a flowchart showing an operation example of the medical imaging apparatus according to the first embodiment.

FIG. 6 is a flowchart showing an example of the operation of the radiation imaging apparatus according to the first embodiment. In FIG. 6, processing starts from a state in which the moving image capturing operation and the still image capturing operation are permitted. In step S601, the communication state comparison unit 205 of the radiation imaging apparatus 101 continues the communication state obtainment processing even when the imaging mode to be permitted after activation has been determined. Subsequently, in step S602, the communication state comparison unit 205 compares the obtained value indicating the communication state (status information indicating the wireless communication state) with the threshold t2. The threshold used for the comparison processing at this time is not the threshold t1 used in the comparison processing in step S404 of FIG. 4 but the threshold t2. The threshold t2 is a communication state threshold corresponding to the minimum wireless communication rate necessary for the moving image capturing operation. If the communication state (status information indicating the wireless communication state) from the comparison result of the communication state comparison unit 205 has a value equal to or larger than the threshold t2, the process returns to step S601 and the communication state comparison unit 205 performs communication state obtainment processing and the comparison processing of step S602. In this case, the operation mode does not change. For example, if the moving image capturing mode is selected as the operation mode, the moving image capturing mode is maintained.

On the other hand, if the communication state (status information indicating the wireless communication state) from the comparison result of the communication state comparison unit 205 in step S602 has a value smaller than the threshold t2 (NO in step S602), the process advances to step S603. When the communication state has a value smaller than the threshold t2, the determination unit 206 permits only the still image capturing operation as the imaging mode and outputs a determination signal indicating the determination result which inhibits the moving image capturing operation to the communication control unit 203 in step S603. The communication control unit 203 controls the wireless communication unit 204 so that the determination signal from the determination unit 206 is transmitted to the control apparatus 104. At this time, the control apparatus 104 controls display of the display unit based on the received determination signal. Since only the still image capturing operation is permitted as the operation mode in the current wireless communication state and the control apparatus 104 is in a state in which the moving image capturing operation cannot be continued due to the change in the communication state, a message prompting the user to stop the moving image capturing operation is displayed on the display unit. Note that if the control apparatus 104 does not receive a determination signal for a predetermined time or more after the determination signal has been received, display control is performed to change the message prompting the user to stop the moving image capturing operation into a non-display state.

In step S604, the determination unit 206 determines whether the moving image capturing operation is being performed. If the moving image capturing operation is not being performed in the determination of step S604 (NO in step S604), the process advances to step S606. In step S606, the determination unit 206 determines the operation mode to be permitted for the current wireless communication state based on the comparison result of the communication state comparison unit 205. If the value indicating the communication state is smaller than the threshold t2, the determination unit 206 inhibits the moving image capturing operation and permits only the still image capturing operation as the operation mode to be permitted in the current wireless communication state. The determination signal indicating the determination result of the determination unit 206 is transmitted from the determination unit 206 to the sensor control unit 202, and it becomes a state in which the still image capturing operation is permitted. Subsequently, in step S607, the radiation imaging apparatus 101 changes to a standby state to wait for an operation instruction from the control apparatus 104.

On the other hand, if the moving image capturing operation is being performed in the determination of step S604 (YES in step S604), the process advances to step S605. In step S605, although the communication state is in a state in which the moving image capturing operation is inhibited, the determination unit 206 determines to continue the moving image capturing operation as the operation mode. The determination signal indicating this determination result is transmitted from the determination unit 206 to the sensor control unit 202, and it becomes a state in which the moving image capturing operation is continued.

The sensor control unit 202 controls the moving image capturing operation of the radiation sensor 201 based on the determination signal from the determination unit 206. When the moving image capturing operation is continued, the sensor control unit 202 of the radiation imaging apparatus 101 continues the imaging operation by changing the image size or the frame rate so that transfer will be possible even if the value indicating the communication state has become smaller than the threshold t2. Alternatively, the sensor control unit 202 can control to continue the imaging operation by changing the image size and the frame rate. The sensor control unit 202 holds, in advance, a lookup table that stores the combinations of image sizes and frame rates settable in the radiation imaging apparatus 101 and the minimum communication state (minimum communication rate) required at that time as shown in FIG. 7. As an example of the communication state (status information indicating the wireless communication state), assume that the communication state is represented as a wireless communication rate. In FIG. 7, settings 702 represent the combinations of settings selectable in the radiation imaging apparatus 101, and settings 701 represent the combinations of settings selectable in the radiation imaging system. The relationship between the settings 701 and the settings 702 is a relationship in which the settings 702 selectable in the radiation imaging apparatus 101 include the settings 701 selectable in the radiation imaging system. Assume that the user can select within the range of the settings 701. Assume also that the threshold t2 is the minimum communication rate (76 Mbps) shown in FIG. 7. If a determination signal indicating that the communication state has a value smaller than the threshold t2 is input from the determination unit 206, the sensor control unit 202 automatically changes the image size or the frame rate in accordance with the current communication state and the lookup table to continue the moving image capturing operation.

Figure 8B:
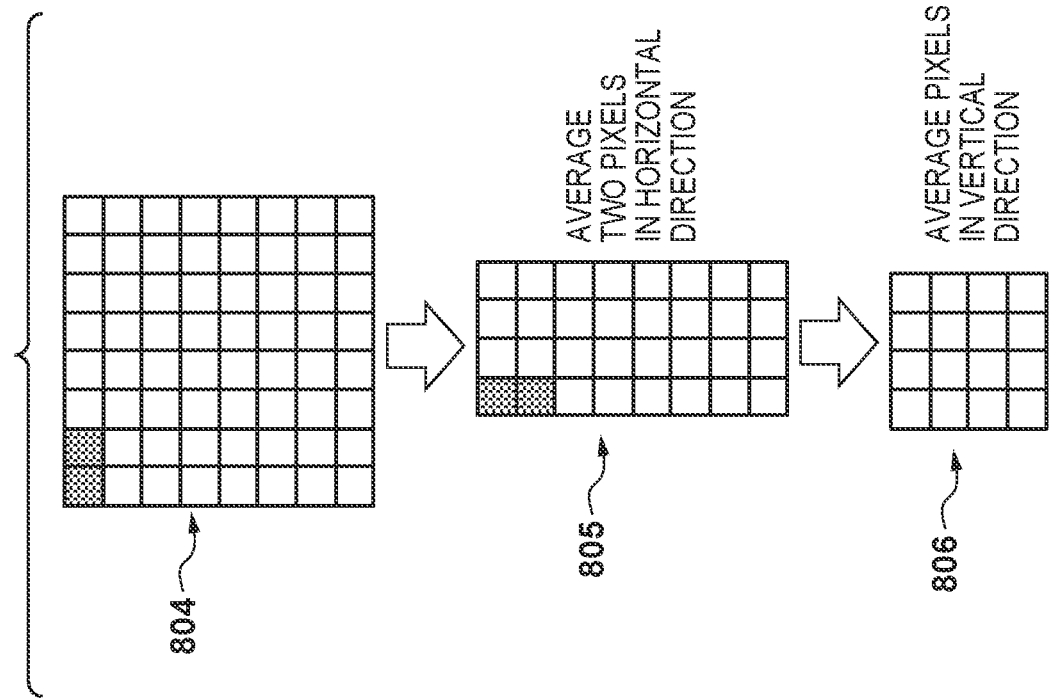
FIGS. 8A and 8B are explanatory views each exemplifying image size change processing according to the first embodiment.
Figure 8A:
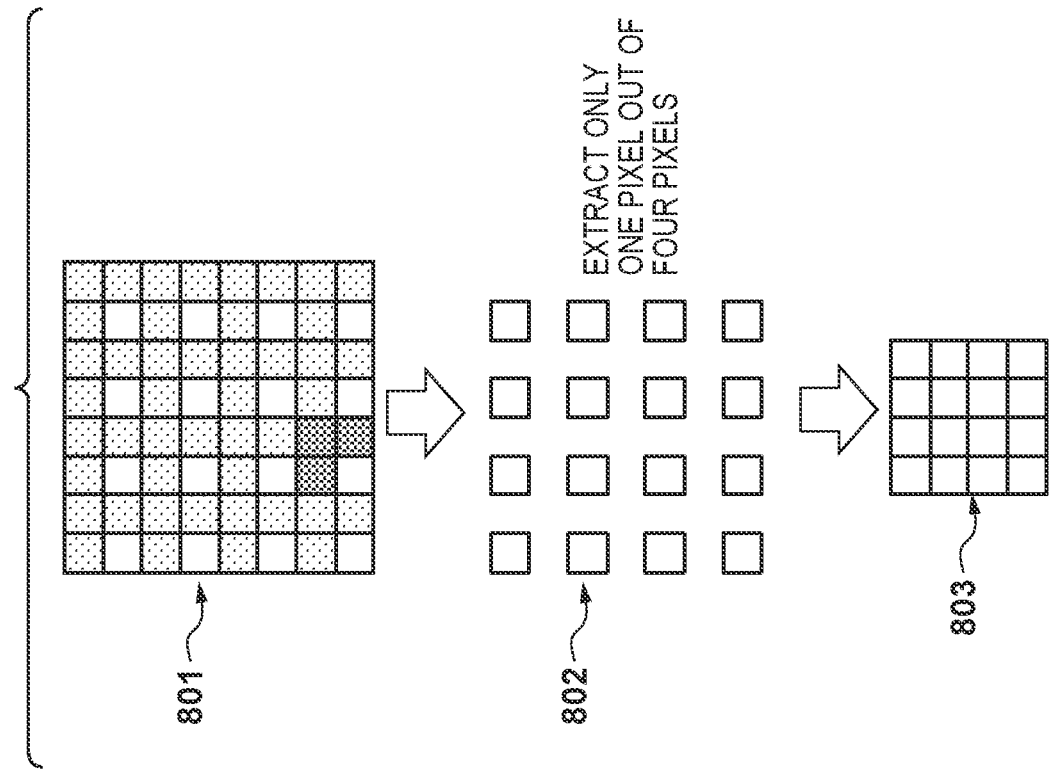

FIGS. 8A and 8B are explanatory views each exemplifying image size change processing (image size reduction processing). FIG. 8A is a view showing an example in which the image size is reduced by thinning out pixels from the readout image data, and FIG. 8B is a view showing an example in which the image size is reduced by averaging pixel values. Note that the respective arrangements of pixel thinning and pixel value averaging are exemplary and are not limited to these examples.

For example, when a reduced image is to be generated by reducing the image size by pixel thinning (FIG. 8A), the sensor control unit 202 reads out pixel data 801 from the radiation sensor 201 and thins out the pixels from the readout pixel data 801. In the example of FIG. 8A, the sensor control unit 202 thins out three pixels on a four-pixel basis in the pixel data 801 and extracts one pixel (pixel data 802). By thinning out three pixels on a four-pixel basis, the size of the pixel data 801 is reduced. Size-reduced pixel data 803 is thus generated by pixel thinning. The hatched portions of the pixel data 801 indicate pixels that are to be thinned out.

When the image size is to be changed by averaging the pixel values (FIG. 8B), the sensor control unit 202 reads out pixel data 804 from the radiation sensor 201 and generates pixel data 805 in which each two pixels in the horizontal direction are averaged with respect to the readout pixel data 804. Out of the pixel data 804 of FIG. 8B, the hatched portions exemplify the two pixels in the horizontal direction that are to be averaged. The sensor control unit 202 performs averaging processing in the same manner for the entire pixel data 804 to generate the pixel data 805. Out of the pixel data 805 of FIG. 8B, the hatched portions exemplify the two pixels in the vertical direction that are to be averaged. The sensor control unit 202 performs averaging processing in the same manner for the entire pixel data 805 to generate pixel data 806. In the example of FIG. 8B, the averaging processing for every two pixels in the vertical direction is performed after the averaging processing for every two pixels in the horizontal direction. However, the present invention is not limited to this example. The averaging processing for every two pixels in the horizontal direction can be performed after the averaging processing for every two pixels in the vertical direction is performed. The size-reduced pixel data 806 is generated by performing averaging processing. The output image size can be reduced by the pixel thinning processing of FIG. 8A and the pixel averaging processing of FIG. 8B. The processes of FIGS. 8A and 8B are not limited to being executed by the sensor control unit 202 and can be performed in the radiation sensor 201.

When the frame rate is to be changed, the sensor control unit 202 of the radiation imaging apparatus 101 notifies, via the communication control unit 203 and the wireless communication unit 204, the radiation generating apparatus 103 of the change in the irradiation timing of radiation. The sensor control unit 202 changes the driving timing of the radiation sensor 201 in correspondence with the output of the irradiation timing change notification of the radiation that will irradiate the radiation sensor 201 (detection unit). If the frame rate is to be decreased, the irradiation dose of the radiation generating apparatus 103 can be increased within a range where the total irradiation dose will not change from before the frame rate is decreased. For example, if the frame rate is halved, the irradiation dose of radiation per one frame can be doubled.

In step S605 of FIG. 6, the process returns to step S602 after the moving image capturing operation is continued. In step S602, the communication state comparison unit 205 compares the obtained value indicating the communication state (status information indicating the wireless communication state) with the threshold t2 and determines the communication state for the second time. If the value indicating the communication state is equal to or larger than the threshold t2 (YES in step S602), the process returns to step S601. The communication state comparison unit 205 performs communication state obtainment processing and the comparison processing of step S602. The determination unit 206 determines the operation mode to be permitted for the current wireless communication state based on the comparison result of the communication state comparison unit 205. If the value indicating the communication state is equal to or larger than the threshold t2 in the communication state determination processing for the third time, the determination unit 206 determines that the operation mode has returned to a wireless communication state in which the moving image capturing operation is permitted. In this case, no determination signal towards the control apparatus 104 is transmitted in step S603 by the determination processing of the determination unit 206 (YES in step S602). When no determination signal is received for a predetermined time or more after having received the determination signal based on the previous determination processing (NO in Step S602, S603), the control apparatus 104 that is displaying a message prompting the user to stop the moving image capturing operation performs display control to change the message to a non-display state. The same processing is repeated after the process returns to step S601.

Note that although the sensor control unit 202 changes the imaging condition so that the imaging condition will have a higher communication rate when the communication state improves, the settings do not automatically transit to settings which require a better communication state than the settings selected by the user. For example, if 76 Mbps is the communication rate selected by the user as an imaging condition, the sensor control unit 202 controls the settings of the imaging conditions in accordance with the communication state up to the selected imaging condition, but will not set imaging conditions beyond the communication rate of 76 Mbps. By controlling the settings of the imaging conditions in this manner, the user can obtain a radiation image matching his/her intention.

Figure 9:
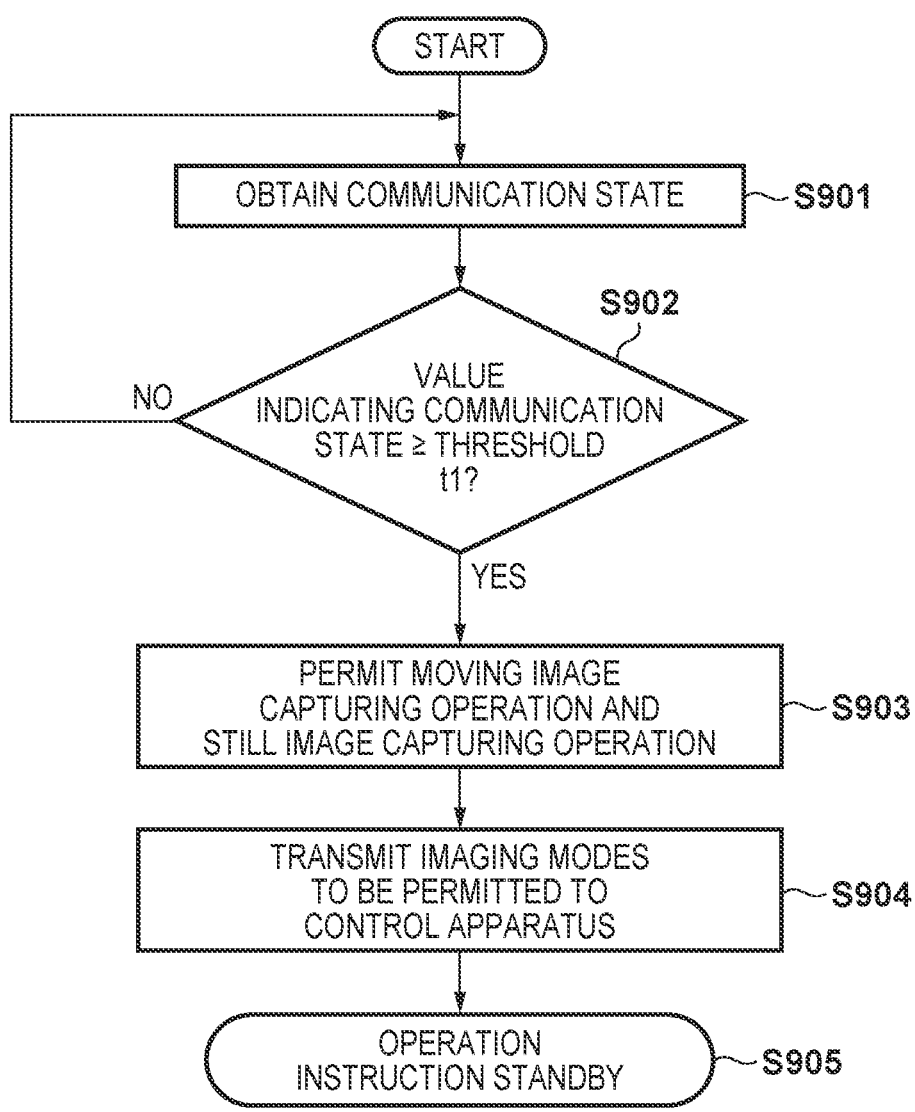
FIG. 9 is a flowchart showing the operation example of the medical imaging apparatus according to the first embodiment.

FIG. 9 is a flowchart showing an example of the operation of the radiation imaging apparatus according to the first embodiment. The sequence of FIG. 9 starts from a state in which only the still image capturing operation is permitted while the moving image capturing operation is inhibited. In step S901, the communication state comparison unit 205 of the radiation imaging apparatus 101 performs communication state obtainment processing even after the imaging mode has been determined. In step S902, the communication state comparison unit 205 compares the obtained value indicating the communication state (status information indicating the wireless communication state) with the threshold t1. If the value indicating the communication state is smaller than the threshold t1 (NO in step S902), the process is returned to step S901 and the communication state comparison unit 205 performs communication state obtainment processing and the comparison processing of step S902.

On the other hand, in step S902, if the communication state (status information indicating the wireless communication state) from the comparison result of the communication state comparison unit 205 has a value equal to or larger than the threshold t1 (YES in step S902), the process advances to step S903.

In step S903, the determination unit 206 determines the operation mode to be permitted for the current wireless communication state based on the comparison result of the communication state comparison unit 205. If the value indicating the communication state is equal to or larger than the threshold t1, the determination unit 206 permits the moving image capturing operation and the still image capturing operation as the operation modes to be permitted for the current wireless communication state.

In step S904, the determination unit 206 outputs a determination signal indicating the determination result to the communication control unit 203. The communication control unit 203 controls the wireless communication unit 204 so that the determination signal from the determination unit 206 is transmitted to the control apparatus 104. Based on the determination signal, the control apparatus 104 sets, as the operation mode of the radiation imaging apparatus, a state in which the moving image capturing operation and the still image capturing operation are permitted as the operation modes to be permitted for the current wireless communication state. In this case, the control apparatus 104 controls the display of the display unit in accordance with the set operation mode of the radiation imaging apparatus. In a state in which the moving image capturing operation is inhibited and only the still image capturing operation is permitted, the display of the display unit is controlled to be the display state shown in FIG. 5B. If the operation mode of the radiation imaging apparatus changes to a state in which the moving image capturing operation and the still image capturing operation are permitted, the control apparatus 104 performs display control so that the display state shown in FIG. 5B becomes the display state shown in FIG. 5A. It becomes possible for the user to select, out of the moving image capturing operation and the still image capturing operation, one imaging mode via the imaging mode selection buttons 503 shown in FIG. 5A. Subsequently, in step S905, the radiation imaging apparatus 101 changes to a standby state to wait for an operation instruction from the control apparatus 104.

According to the arrangement of the first embodiment, the moving image capturing operation can be continued even when the wireless communication state varies after the moving image capturing operation is permitted and started. Since a desired moving image capturing operation can be performed without inhibiting the moving image capturing operation even when the wireless communication state varies, a radiation imaging technique that is highly convenient for the user can be provided.

Second Embodiment

An arrangement which includes a plurality of moving image capturing modes having different thresholds corresponding to the communication rates necessary for the moving image capturing operations of the moving image capturing modes, respectively, and switches between the moving image capturing modes in accordance with the communication state will be described in the second embodiment. The arrangement of a radiation imaging system is the same as the first embodiment. A radiation imaging apparatus 101 can perform a still image capturing operation and a moving image capturing operation in a plurality of types of modes. A threshold is set for each moving image capturing mode. A communication state comparison unit 205 obtains status information that indicates the wireless communication state obtained at the time of wireless communication operation of a wireless communication unit 204 and compares the status information with a predetermined threshold set for each moving image capturing mode. Based on the comparison result of the communication state comparison unit 205, a determination unit 206 determines the operation mode permitted for the current wireless communication state and outputs the determination result to a sensor control unit 202 and a communication control unit 203.

FIG. 10 is a view exemplifying the relationships between the plurality of moving image capturing modes and the thresholds set for the respective moving image capturing modes. In the radiation imaging system according to the second embodiment, assume that there are three types of moving image capturing modes, mode A, mode B, and mode C as the moving image capturing modes. The three types of moving image modes, mode A, mode B, and mode C, each have a different image size and frame rate, and the minimum frame rate necessary for executing a corresponding moving image capturing operation also differs for each moving image capturing mode. Assume that the wireless communication rates required by the respective moving image capturing modes have a relationship in which mode C>mode B>mode A.

In the radiation imaging system, a threshold t2 301 is a communication state threshold corresponding to the minimum wireless communication rate necessary for the moving image capturing operation in mode A, and a threshold t1 302 is a communication state threshold obtained by adding a predetermined margin to the threshold t2 301.

A threshold tB2 1001 is a communication state threshold corresponding to the minimum wireless communication rate necessary for the moving image capturing operation in mode B. A threshold tB1 1002 is a communication state threshold obtained by adding a predetermined margin to the threshold tB2 1001. In a similar manner, a threshold tC2 1003 is a communication state threshold corresponding to the minimum wireless communication rate necessary for the moving image capturing operation in mode C. A threshold tC1 1004 is a communication state threshold obtained by adding a predetermined margin to the threshold tC2 1003. Each margin corresponds to the predicted communication state variation range. The margins of the respective moving image capturing modes may be the same value or be set separately with appropriate values. The relative magnitude relationship of the thresholds is threshold tC1>threshold tC2>threshold tB1>threshold tB2>threshold t1>threshold t2. When the value indicating the communication state is smaller than the threshold t2 301, the radiation imaging system (radiation imaging apparatus 101) cannot perform the moving image capturing operation and can only perform the still image capturing operation.

FIG. 11 is a flowchart showing an example of the operation of the radiation imaging apparatus according to the second embodiment. FIG. 11 shows the operation immediately after activation of the radiation imaging apparatus 101. The radiation imaging apparatus 101 is activated in step S1101. In step S1102, the communication control unit 203 of the radiation imaging apparatus 101 controls the wireless communication unit 204 and establishes wireless communication with a preset connection destination.

In step S1103, the communication state comparison unit 205 of the radiation imaging apparatus 101 obtains the status information indicating the wireless communication state from the wireless communication unit 204 as communication state obtainment processing. In step S1104, the communication state comparison unit 205 compares the obtained value indicating the communication state (status information indicating the wireless communication state) with the threshold t1. The determination unit 206 determines the operation modes to be permitted for the current wireless state based on the comparison result of the communication state comparison unit 205. If the communication state (status information indicating the wireless communication state) from the comparison result of the communication state comparison unit 205 in step S1104 has a value smaller than the threshold t1 (NO in step S1104), the process advances to step S1105. In step S1105, the determination unit 206 determines the operation modes to be permitted for the current wireless communication state based on the comparison result of the communication state comparison unit 205. If the value indicating the communication state is smaller than the threshold t1, the determination unit 206 inhibits the moving image capturing operation and only permits the still image capturing operation as the operation mode to be permitted for the current wireless communication state. A determination signal indicating the determination result of the determination unit 206 is transmitted from the determination unit 206 to the sensor control unit 202, and it becomes a state in which still image capturing operation is permitted.

On the other hand, if the communication state (status information indicating the wireless communication state) from the comparison result of the communication state comparison unit 205 in step S1104 has a value equal to or larger than the threshold t1 (YES in step S1104), the process advances to step S1106. In step S1106, the communication state comparison unit 205 compares the obtained value indicating the communication state (status information indicating the wireless communication state) with the threshold tB1. The determination unit 206 determines the operation modes to be permitted for the current wireless communication state based on the comparison result of the communication state comparison unit 205. If the communication state (status information indicating the wireless communication state) from the comparison result of the communication state comparison unit 205 has a value smaller than the threshold tB1 (NO in step S1106), the process advances to step S1107.

In step S1107, the determination unit 206 determines the operation modes to be permitted for the current wireless communication state based on the comparison result of the communication state comparison unit 205. If the value indicating the communication state is equal to or larger than the threshold t1 but smaller than the threshold tB1, the determination unit 206 permits the still image capturing operation and the moving image capturing operation (mode A) as the operation modes to be permitted for the current wireless communication state. The determination signal indicating the determination result of the determination unit 206 is transmitted from the determination unit 206 to the sensor control unit 202, and it becomes a state in which the still image capturing operation and the moving image capturing operation (mode A) are permitted.

If the communication state (status information indicating the wireless communication state) from the comparison result of the communication state comparison unit 205 in step S1106 has a value equal to or larger than the threshold tB1 (YES in step S1106), the process advances to step S1108. In step S1108, the communication state comparison state 205 compares the obtained value indicating the communication state (status information indicating the wireless communication state) with the threshold tC1. The determination unit 206 determines the operation modes to be permitted for the current wireless communication state based on the comparison result of the communication state comparison unit 205. If the communication state (status information indicating the wireless communication state) from the comparison result of the communication state comparison unit 205 has a value smaller than the threshold tC1 (NO in step S1108), the process advances to step S1109.

In step S1109, the determination unit 206 determines the operation modes to be permitted for the current wireless communication state based on the comparison result of the communication state comparison unit 205. If the value indicating the communication state is equal to or larger than the threshold tB1 but smaller than the threshold tC1, the determination unit 206 permits the still image capturing operation and the moving image capturing operations (modes A and B) as the operation modes to be permitted for the current wireless communication state. The determination signal indicating the determination result of the determination unit 206 is transmitted from the determination unit 206 to the sensor control unit 202, and it becomes a state in which the still image capturing operation and the moving image capturing operations (modes A and B) are permitted.

If the communication state (status information indicating the wireless communication state) from the comparison result of the communication state comparison unit 205 in step S1108 has a value equal to or larger than the threshold tC1 (YES in step S1108), the process advances to step S1110. In step S1110, the determination unit 206 determines the operation modes to be permitted for the current wireless communication state based on the comparison result of the communication state comparison unit 205. If the value indicating the communication state is equal to or larger than the threshold tC1, the determination unit 206 permits the still image capturing operation and the moving image capturing operations (modes A, B, and C) as the operation modes to be permitted for the current wireless communication state. The determination signal indicating the determination result of the determination unit 206 is transmitted from the determination unit 206 to the sensor control unit 202, and it becomes a state in which the still image capturing operation and all the modes of the moving image capturing operations (modes A, B, and C) are permitted.

In step S1111, the determination unit 206 outputs the determination signal indicating the determination result to the communication control unit 203. The communication control unit 203 controls the wireless communication unit 204 so that the determination signal from the determination unit 206 is transmitted to a control apparatus 104. The control apparatus 104 sets the operation modes to be permitted for the current wireless communication state based on the determination signal. In step S1112, the radiation imaging apparatus 101 changes to a standby state to wait for an operation instruction from the control apparatus 104.

Figure 12A:
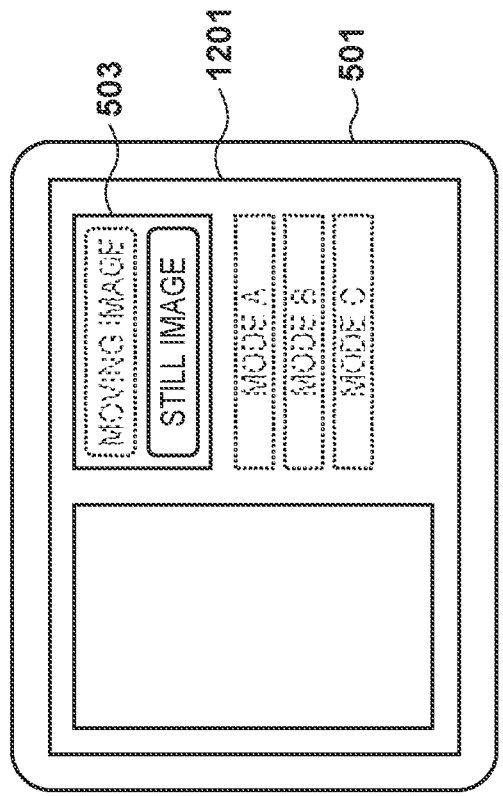
FIGS. 12A to 12D are views each showing an example of a display unit screen according to the second embodiment.

Processing of the control apparatus 104 upon reception of the determination signal will be described next. Based on the determination signal received from the radiation imaging apparatus 101, the control apparatus 104 controls the display of a display unit 501 of the control apparatus 104. FIGS. 12A to 12D are views each showing an example of the screen of the display unit 501. The control apparatus 104 displays a console screen 1201 for controlling the radiation imaging apparatus 101 on the display unit 501. FIG. 12A shows a state in which the still image capturing operation is permitted as the operation mode of the radiation imaging apparatus 101. Imaging mode selection buttons 503 are selection units for selecting an imaging mode. In FIG. 12A, the user can select only the still image capturing operation via the imaging mode selection buttons 503. The selection buttons concerning moving images are all grayed out, and none of the moving image capturing operations (modes A, B, and C) can be selected by the user via the imaging mode selection buttons 503. The display screen of FIG. 12A is based on the determination result of the determination unit 206 in step S1105 of FIG. 11.

Figure 12B:
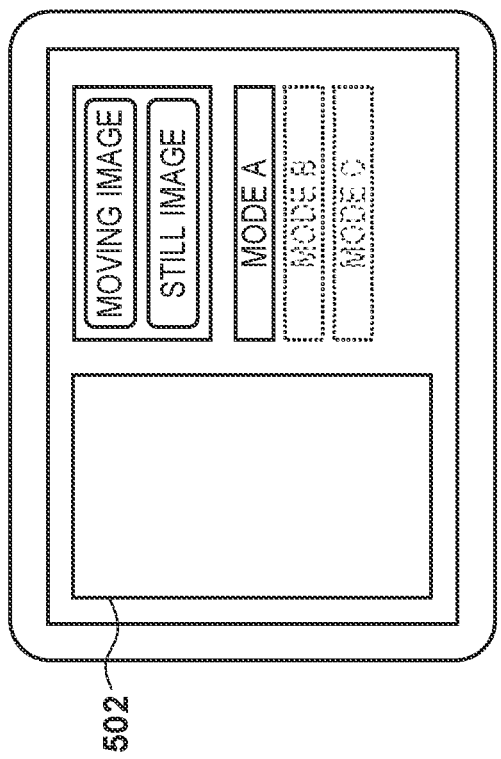

FIG. 12B shows a state in which the still image capturing operation and the moving image capturing operation (mode A) have been permitted as the operation modes of the radiation imaging apparatus 101. The user can select the still image capturing operation and the moving image capturing operation (mode A) via the imaging mode selection buttons 503. Out of the moving image capturing modes, the imaging mode selection buttons for mode B and mode C have been grayed out, and mode B and mode C cannot be selected by the user via the imaging mode selection buttons 503. The display screen of FIG. 12B is based on the determination result of the determination unit 206 in step S1107 of FIG. 11.

Figure 12C:
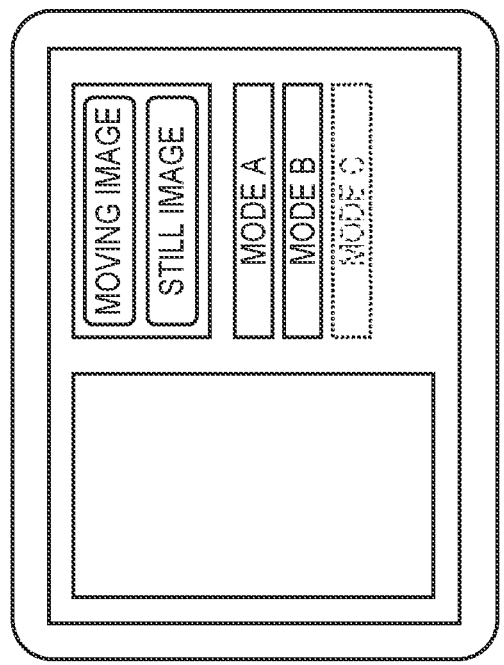

FIG. 12C shows a state in which the still image capturing operation and the moving image capturing operations (modes A and B) have been permitted as the operation modes of the radiation imaging apparatus 101. The user can select the still image capturing operation and the moving image capturing operations (modes A and B) via the imaging mode selection buttons 503. Out of the moving image capturing modes, the imaging mode selection button for mode C has been grayed out and mode C cannot be selected by the user via the imaging mode selection buttons 503. The display screen of FIG. 12C is based on the determination result of the determination unit 206 in step S1109 of FIG. 11.

Figure 12D:
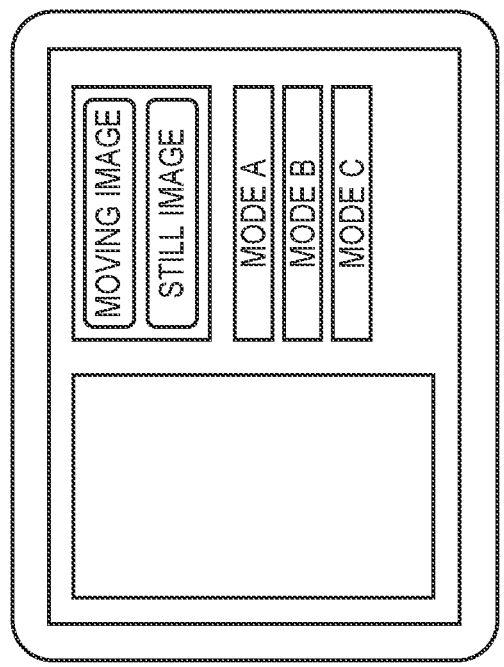

FIG. 12D shows a state in which the still image capturing operation and all the moving image capturing operations (modes A, B, and C) have been permitted as the operation modes of the radiation imaging apparatus 101. The user can select the still image capturing operation and all the moving image capturing operations (modes A, B, and C) via the imaging mode selection buttons 503. The display screen of FIG. 12D is based on the determination result of the determination unit 206 in step S1110 of FIG. 11.

When the user selects the imaging mode selection buttons, the processing advances to the imaging sequences corresponding to the respective imaging modes. If the user selects the moving image capturing operations, the control apparatus 104 selects the frame rate, the image size, irradiation conditions, and the like in accordance with the selection operation. Based on the selected imaging conditions, a radiation tube 102 and a radiation generating apparatus 103 generate radiation and perform irradiation, and the radiation imaging apparatus 101 starts imaging. In the moving image capturing operations, pulse imaging in which images are obtained in accordance with the pulses of radiation irradiating the object and continuous imaging in which the object is continuously irradiated with radiation can be executed. If the user selects the still image capturing operation, the control apparatus 104 selects the irradiation conditions, an imaging region, and the like in accordance with the user selection operation, and the radiation imaging apparatus 101 starts imaging.

FIG. 13 is a flowchart showing an example of the operation of the radiation imaging apparatus according to the second embodiment. FIG. 13 starts the processing from a state in which the moving image capturing operations (mode A and mode B) and the still image capturing operation have been permitted.

In step S1301, the communication state comparison unit 205 of the radiation imaging apparatus 101 continues the communication state obtainment processing even after the imaging modes to be permitted after activation have been determined. Subsequently, in step S1302, the communication state comparison unit 205 compares the obtained value indicating the communication state (status information indicating the wireless communication state) with the threshold tB2. If the communication state from the comparison result of the communication state comparison unit 205 has a value equal to or larger than the threshold tB2 (YES in step S1302), the process returns to step S1301 and the communication state comparison unit 205 performs the communication state obtainment processing and the comparison processing of step S1302. In this case, the operation modes are not changed. For example, if the moving image capturing operation (mode A) is selected as the operation mode, the moving image capturing operation (mode A) is maintained. In this case no determination signal indicating the determination result of the determination unit 206 is transmitted from the radiation imaging apparatus 101 to the control apparatus 104.

On the other hand, if the communication state (status information indicating the wireless communication state) from the comparison result of the communication state comparison unit 205 in step S1302 has a value smaller than the threshold tB2 (NO in step S1302), the process advances to step S1303. In step S1303, if the communication state has a value smaller than the threshold tB2, the communication state comparison unit 205 compares the obtained value indicating the communication state (status information indicating the wireless communication state) with the threshold t2.

In step S1303, if the communication state (status information indicating the wireless communication state) from the comparison result of the communication state comparison unit 205 in step S1303 has a value smaller than the threshold t2 (NO in step S1303), the process advances to step S1304. In step S1304, if the communication state has a value smaller than the threshold t2, the determination unit 206 outputs the determination signal indicating the determination result that permits only the still image capturing operation and inhibits the moving image capturing operation (mode A) as the operation modes to the communication control unit 203. The communication control unit 203 controls the wireless communication unit 204 so that the determination signal from the determination unit 206 is transmitted to the control apparatus 104. At this time, the control apparatus 104 controls the display of display unit based on the received determination signal.

If the communication state (status information indicating the wireless communication state) from the comparison result of the communication state comparison unit 205 in step S1303 has a value equal to or larger than the threshold t2 (YES in step S1303), the process advances to step S1305. In step S1305, if the value indicating the communication state is smaller than the threshold tB2 and is equal to or larger than the threshold t2, the determination unit 206 outputs a determination signal permitting the still image capturing operation and the moving image capturing operation (mode A) and inhibiting the moving image capturing operation (mode B) as the operation modes to the communication control unit 203. The communication control unit 203 controls the wireless communication unit 204 so that the determination signal from the determination unit 206 is transmitted to the control apparatus 104. At this time, the control apparatus 104 controls the display of the display unit based on the received determination signal.

In step S1306, the determination unit 206 determines whether a moving image capturing operation is being performed. If it is determined that no moving image capturing operation is being performed (NO in step S1306), the process advances to step S1308. In step S1308, the determination unit 206 determines the operation mode to be permitted for the current wireless communication state based on the comparison result of the communication state comparison unit 205. The determination unit 206 permits only the operation mode permitted for the current wireless communication state. The determination signal indicating the determination result of the determination unit 206 is transmitted from the determination unit 206 to the sensor control unit 202. Subsequently, in step S1308, the radiation imaging apparatus 101 changes to a standby state to wait for an operation instruction from the control apparatus 104.

On the other hand, if it is determined that a moving image capturing operation is being performed (YES in step S1306), the process advances to step S1307. In step S1307, the determination unit 206 determines to continue the moving image capturing operation as the operation mode. If the moving image capturing operation (mode B) has been inhibited in the preceding step S1305, the determination unit 206 determines to continue the moving image capturing operation in the moving image capturing operation (mode A). The determination signal indicating this determination result is transmitted from the determination unit 206 to the sensor control unit 202, and it becomes a state in which the moving image capturing operation is continued. The sensor control unit 202 controls the moving image capturing operation in a radiation sensor 201 based on the determination signal from the determination unit 206. If imaging is being performed in the moving image capturing operation (mode B), the moving image capturing mode is automatically changed from the moving image capturing operation (mode B) to the moving image capturing operation (mode A) and the moving image capturing operation is continued. The moving image capturing mode change is not limited to changing from mode B to mode A. The moving image capturing mode can be set in a range where the communication state (status information indicating the wireless communication state) has a value smaller than the threshold tB2 and equal to or larger than the threshold t2.

When the moving image capturing operation is continued, the sensor control unit 202 of the radiation imaging apparatus 101 continues the imaging operation by changing the image size or the frame rate so that transfer will be possible even if the value indicating the communication state has become smaller than the threshold t2. Alternatively, the sensor control unit 202 can perform control so as to continue the imaging operation by changing the image size and the frame rate.

In addition, if the moving image capturing operation is inhibited and only the still image capturing operation is permitted in the preceding step S1304, the determination unit 206 determines to continue the moving image capturing operation as the operation mode although the current communication state is a state in which the moving image capturing operation should be inhibited. The determination signal indicating this determination result is transmitted from the determination unit 206 to the sensor control unit 202, and it becomes a state in the moving image capturing operation is continued. The sensor control unit 202 controls the radiation sensor 201 based on the determination signal from the determination unit 206 and the imaging conditions from the communication control unit 203. When the moving image capturing operation is continued, the sensor control unit 202 of the radiation imaging apparatus 101 continues the imaging operation by changing the image size or the frame rate so that transfer will be possible even if the value indicating the communication has become smaller than the threshold t2. Alternatively, the sensor control unit 202 can perform control so as to continue the imaging operation by changing the image size and the frame rate. This processing is the same as the first embodiment.

The communication control unit 203 controls the wireless communication unit 204 so that the determination signal from the determination unit 206 is transmitted to the control apparatus 104. At this time, based on the received determination signal, the control apparatus 104 controls the display of the display unit 501 as in the examples of the screens shown in FIGS. 12A to 12D.

After the moving image capturing operation is continued in step S1307, the process returns to step S1302. In step S1302, the communication state comparison unit 205 compares the obtained value indicating the communication state (status information indicating the wireless communication state) with the threshold tB2 and determines the communication state for the second time. If the value indicating the communication state is equal to or larger than the threshold tB2 (YES in step S1302), the process returns to step S1301. The communication state comparison unit 205 performs communication state obtainment processing and the comparison processing in step S1302. The same processes are repeated for step S1302 and subsequent steps. Note that if the communication state improves, the sensor control unit 202 changes the settings of the imaging conditions into imaging conditions of a higher communication rate, but the settings do not automatically transit to settings that require a better communication state than the settings selected by the user.

According to the arrangement of the second embodiment, even when the wireless communication state varies after the moving image capturing operation is permitted and started, the moving image capturing operation can continue by changing to a moving image capturing mode having different imaging conditions. Since a desired moving image capturing operation can be performed without inhibiting the moving image capturing operation even when the wireless communication state varies, a radiation imaging technique that is highly convenient for the user can be provided.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-255441, filed Dec. 17, 2014, which is hereby incorporated by reference herein in its entirety.

What is claimed is:

1. A radiation imaging apparatus comprising:
a radiation sensor, which has a plurality of pixels, for receiving radiation that has passed through an object and generating digital data;
one or more processors; and
a memory having instructions store thereon which when executed by the one or more processors, cause the radiation imaging apparatus to:
function as an interface for wireless communication with another apparatus and transmit image data based on the digital data read out from the radiation sensor;
obtain state information indicating a communication state of the wireless communication, which is information indicating quality of communication state of the wireless communication which is calculated based on at least one of reception intensity of radio receivable by the wireless communication, a communication rate which is an amount of data capable of being transmitted per unit time and is calculated at a time of transmission of data to a transmission destination, or an error rate; and
control driving of the radiation sensor for reading out the digital data from the radiation sensor to generate the image data,
wherein the driving of the radiation sensor is controlled so that the driving of the radiation sensor for a moving image capturing operation is started in a case that the state information is equal to or larger than a first threshold obtained by adding a variation range of the communication state to a second threshold corresponding to a communication rate necessary for the moving image capturing operation, and
wherein the driving of the radiation sensor is controlled so that the driving of the radiation sensor for the moving image capturing operation is maintained in a case that the state information is equal to or larger than the first threshold, or the state information is smaller than the first threshold and the state information is equal to or larger than the second threshold during the moving image capturing operation.

2. The radiation imaging apparatus according to claim 1, wherein in a case that the state information becomes smaller than the second threshold during the moving image capturing operation, the driving of the radiation sensor is controlled so as to read out digital data to be image data in which pixels are thinned out.

3. The radiation imaging apparatus according to claim 1, wherein in a case that the state information becomes smaller than the second threshold during the moving image capturing operation, the driving of the radiation sensor is controlled so as to decrease a frame rate of the moving image capturing operation.

4. The radiation imaging apparatus according to claim 1, wherein in a case that the state information after activation of the radiation imaging apparatus becomes smaller than the second threshold and the radiation imaging apparatus does not perform the moving image capturing operation, the driving of the radiation sensor for the moving image capturing operation is inhibited and the driving of the radiation sensor for a still image capturing operation is started, and
wherein in a case that the state information after activation is smaller than the second threshold and the radiation imaging apparatus performs the moving image capturing operation, the driving of the radiation sensor is controlled so as to continue the moving image capturing operation by generating a reduced image which has a reduced image data size or decreasing a frame rate of the moving image capturing operation.

5. The radiation imaging apparatus according to claim 1, wherein in a case that the state information at activation of the radiation imaging apparatus is equal to or larger than the first threshold, the driving of the radiation sensor for the moving image capturing operation and the driving of the radiation sensor for a still image capturing operation are permitted, and
wherein in a case that the state information at activation is smaller than the first threshold, the driving of the radiation sensor is controlled so that the driving of the radiation sensor for the moving image capturing operation is inhibited and the driving of the radiation sensor for the still image capturing operation is permitted.

6. The radiation imaging apparatus according to claim 1, wherein the radiation imaging apparatus has, as modes of the moving image capturing operation, a plurality of moving image capturing modes set with different first and second threshold values, respectively, and
wherein in a case that the state information becomes smaller than the second threshold of a first moving image capturing mode during a moving image capturing operation by the first moving image capturing mode, the driving of the radiation sensor for the moving image capturing operation by the first moving image capturing mode is inhibited and the driving of the radiation sensor to perform the moving image capturing operation by a second moving image capturing mode having a communication rate lower than in the first moving image capturing mode is controlled.

7. The radiation imaging apparatus according to claim 2, wherein a lookup table storing a settable image size and frame rate combination and a communication rate are stored in the memory, and
wherein generation of a reduced image is controlled based on the state information and the lookup table.

8. The radiation imaging apparatus according to claim 1, wherein the variation range of the communication state is set based on a result of a measurement of the state information measured in advance.

9. The radiation imaging apparatus according to claim 1, wherein at least one of the reception intensity, the communication rate, and the error rate, is used, as the state information, for the comparison with one of the first threshold and the second threshold, is used.

10. The radiation imaging apparatus according to claim 1, wherein an operation mode to be permitted in the state information is determined based on the result of the comparison with the communication state and a result of a determination is outputted via the wireless communication.

11. The radiation imaging apparatus according to claim 10, further comprising:
a display which displays the operation mode to be permitted in the communication state of the wireless communication indicated by the state information,
wherein the display is controlled based on a result of a determination of the operation mode.

12. A radiation imaging system comprising:
a radiation imaging apparatus according to claim 1; and
a processor that controls an operation state of the radiation imaging apparatus and processes image data generated by the radiation imaging apparatus,
wherein the processor includes a display which displays an operation mode to be permitted in a communication state with the radiation imaging apparatus.

13. An imaging control method of a radiation imaging apparatus that includes: a radiation sensor, which has a plurality of pixels, for receiving radiation that has passed through an object and generating a digital data, one or more processors, and a memory having instructions stored thereon which when executed by the one or more processor, cause the radiation imaging apparatus to function as an interface for wireless communication with another apparatus and transmit image data based on the digital data read out from the radiation sensor, obtain state information indicating a communication state of the wireless communication, and control driving of the radiation sensor for reading out the digital data from the radiation sensor to generate the image data, the imaging control method comprising:
obtaining state information indicating a communication state of the wireless communication from, which is information indicating quality of communication state of the wireless communication which is calculated based on at least one of reception intensity of radio receivable by the wireless communication, a communication rate which is an amount of data capable of being transmitted per unit time and is calculated at a time of transmission of data to a transmission destination, or an error rate; and
controlling driving of the radiation sensor,
wherein the driving of the radiation sensor is controlled so that the driving of the radiation sensor for a moving image capturing operation is started in a case that the state information is equal to or larger than a first threshold obtained by adding a variation range of the communication state to a second threshold corresponding to a communication rate necessary for the moving image capturing operation, and
wherein the driving of the radiation sensor is controlled so that the driving of the radiation sensor for the moving image capturing operation is maintained in a case that the state information is equal to or larger than the first threshold, or the state information is smaller than the first threshold and the state information is equal to or larger than the second threshold during the moving image capturing operation.

* * * * *